US011279952B2

(12) United States Patent
Sondermeijer et al.

(10) Patent No.: US 11,279,952 B2
(45) Date of Patent: Mar. 22, 2022

(54) RECOMBINANT EXPRESSION OF PCV2B ORF2 PROTEIN IN INSECT CELLS

(71) Applicant: Intervet Inc., Madison, NJ (US)

(72) Inventors: Paulus Jacobus Antonius Sondermeijer, Boxmeer (NL); Lisette Sanders, Bergen (NL); Karin Huberdina Antonia Van Der Heijden-Liefkens, Veghel (NL)

(73) Assignee: Intervet Inc., Madison, NJ (US)

( * ) Notice: Subject to any disclaimer, the term of this patent is extended or adjusted under 35 U.S.C. 154(b) by 36 days.

(21) Appl. No.: 16/756,490

(22) PCT Filed: Oct. 16, 2018

(86) PCT No.: PCT/EP2018/078189
§ 371 (c)(1),
(2) Date: Apr. 16, 2020

(87) PCT Pub. No.: WO2019/076864
PCT Pub. Date: Apr. 25, 2019

(65) Prior Publication Data
US 2020/0299726 A1    Sep. 24, 2020

(30) Foreign Application Priority Data

Oct. 17, 2017   (EP) .................... 17196768

(51) Int. Cl.
| C12N 15/86 | (2006.01) |
| C12N 5/07 | (2010.01) |
| C12N 7/00 | (2006.01) |
| A61K 39/12 | (2006.01) |
| A61K 39/39 | (2006.01) |
| A61P 31/20 | (2006.01) |
| A61K 39/00 | (2006.01) |

(52) U.S. Cl.
CPC ............. *C12N 15/86* (2013.01); *A61K 39/12* (2013.01); *A61K 39/39* (2013.01); *A61P 31/20* (2018.01); *C12N 5/0601* (2013.01); *C12N 7/00* (2013.01); *A61K 2039/5258* (2013.01); *A61K 2039/552* (2013.01); *C12N 2510/00* (2013.01); *C12N 2750/10022* (2013.01); *C12N 2750/10023* (2013.01); *C12N 2750/10034* (2013.01); *C12N 2750/10051* (2013.01)

(58) Field of Classification Search
None
See application file for complete search history.

(56) References Cited

U.S. PATENT DOCUMENTS 7,910,306 B2    3/2011  Eichmeyer et al.
2020/0299726 A1*  9/2020  Sondermeijer ..........  C12N 7/00

FOREIGN PATENT DOCUMENTS

| KR | 20160058958 A | 5/2016 |
| WO | 2009/000459 A1 | 12/2008 |
| WO | 2010068969 A1 | 6/2010 |
| WO | 2014134561 A2 | 9/2014 |
| WO | 2015/048115 A1 | 4/2015 |
| WO | 2015/051099 A1 | 4/2015 |
| WO | 2019025519 A1 | 2/2019 |

OTHER PUBLICATIONS

Davies et al. (Virus Research. 2016; 217: 32-37).*
Wang et al. (Research in Veterinary Science. 2013; 94: 789-795).*
Wei et al. (Virus Evolution. 2019; 5 (2): vez026).*
Yu et al. (Vaccine. 2016; 34: 6358-6366).*
Afghah, Z. et al., Ten years of PCV2 vaccines and vaccination: Is eradication a possibility?, Veterinary Microbiology, 2017, pp. 21-28, 206.
European Search report for application No. 17196768.0, dated Apr. 6, 2018, 11 pages.
Franzo, G. et al., Porcine circovirus type 2 (PCV2) evolution before and after the vaccination introduction: A large scale epidemiological study, Nature, 2016, srep39458, pp. 1-10, 6.
GenBank AF055392.1, Porcine circovirus 2 from Canada, complete genome, (1998), 3 pages.
GenBank AF055394.1, Porcine circovirus 2 from France, complete genome, (1998), 3 pages.
GenBank JX512856.1, Porcine circovirus 2 isolate S99-1542/3a, complete genome, (2012), 2 pages.
Gillespie, J. et al., Porcine circovirus type 2 and porcine circovirus-associated disease, J Vet Intern Med, 2009, pp. 1151-1163, 23.
International Search Report for PCT/EP2018/078189, dated Nov. 29, 2018, 17 pages.
Karuppannan, A et al, Porcine Circovirus Tyoe 2 (PCV2) Vaccines in the Context of Current Molecular Epidemiology, Viruses, 2017, pp. 1-15, vol. 9, 99.
López-Vidal, J. et al., Improved Production Efficiency of Virus-Like Paticles by the Baulovirus Expression Vector System, PLOS One, 2015, pp. 1-13, DOI:10.1371/journal.pone.0140039.

(Continued)

*Primary Examiner* — Shanon A. Foley
(74) *Attorney, Agent, or Firm* — Michael D. Davis

(57) ABSTRACT

The present invention relates to the field of veterinary vaccines, in particular to porcine vaccines against PCV2 and associated diseases. Specifically the invention relates to the finding that a mutation is required in PCV2b ORF2 protein, to prevent its nuclear accumulation upon expression in insect cells; the mutation introduces a Proline at amino acid position 131. This allows efficient expression in insect cells, easy harvesting, and generates large amounts of virus-like particles. The VLPs are highly effective in vaccines for porcines for reduction of infection by PCV2 or of associated signs of disease.

13 Claims, 2 Drawing Sheets
Specification includes a Sequence Listing.

(56) References Cited

OTHER PUBLICATIONS

Saha, D. et al., Single amino acid mutations in the capsid switch the neutralization phenotype of porcine circovirus 2, Journal of General Virology, 2012, pp. 1548-1555, 93.
Segales, J. et al., PCV-2 genotype definition and nomenclature, Veterinary Record, 2008, pp. 867-868, 162.
Shen, H-G., et al., Prevalence and phylogenetic analysis of the current porcine circovirus 2 genotyes after implementation of widespread vaccination programmes in the USA, Journal of General Virology, 2012, pp. 1345-1355, 93.

* cited by examiner

Figure 3

IHC score after PCV2b challenge

Figure 4

IHC score after PCV2d challenge

RECOMBINANT EXPRESSION OF PCV2B ORF2 PROTEIN IN INSECT CELLS

CROSS-REFERENCE TO RELATED APPLICATIONS

This application is a national stage entry under 35 U.S.C. § 371 of PCT/EP2018/078189, filed on Oct. 16, 2018, which claims priority to EP17196768.0, filed on Oct. 17, 2017, the content of PCT/EP2018/078189 is hereby incorporated by reference in its entirety.

The present invention relates to the field of veterinary vaccines, in particular to porcine vaccines for PCV2. Specifically the invention relates to insect cells comprising a heterologous nucleic acid sequence expressing a mutant PCV2b ORF2 protein, to virus-like particles of the mutant PCV2b ORF2 protein, to methods for production or use of the insect cells or of the mutant PCV2b ORF2 protein, and to vaccines for porcine animals.

Porcine circovirus 2 (PCV2) is a pathogen of porcine animals, occurring worldwide and causing much animal suffering, and severe economic losses to the agricultural sector. For a review see Gillespie et al. (2009, J. Vet. Intern. Med., vol. 23, p. 1151-1163).

PCV2 belongs to the family of Circoviridae, and has a small (17 nm) icosahedral non-enveloped virion, containing a circular, single stranded DNA genome of about 1.76 kb. The genome contains only a few open reading frames, of which ORF2 encodes the viral capsid protein that contains the main virus-neutralising epitopes.

PCV2 is relatively stable, and highly infectious. It is shed via different kinds of body-secretions, and can spread both horizontally and vertically in a swine herd. The main lesions caused by PCV2 infection are lymphoid depletions; the resulting immunosuppression also makes an infected animal susceptible to secondary- or concurrent infections. Consequently PCV2 is involved in a number of swine disease syndromes which are collectively named: porcine circovirus associated disease (PCVAD). The most pronounced PCVAD is the "postweaning multisystemic wasting syndrome" (PMWS), observed in young swine. The clinical signs and pathology of PMWS include progressive wasting, dyspnea, tachypnea, and occasionally icterus and jaundice. Other PCVAD's are: Porcine Respiratory Disease Complex, Porcine Dermatitis and Nephropathy Syndrome, reproductive failure, granulomatous enteritis, congenital tremors, and exudative epidermitis. For reviews see: the Merck Veterinary Manual, 11$^{th}$ ed., 2016, ISBN: 9780911910933; and: "Diseases of Swine", 10$^{th}$ ed., 2012, ISBN: 9780813822679.

Without a secondary infection however, the majority of PCV2 infected swine may not show clear clinical symptoms of disease, except for poor growth and -performance in apparently healthy swine. (Sub-)Clinical symptoms of PCVAD caused by PCV2 can be observed in swine usually from 3 or 4 weeks of age onwards, which is the time at which the piglets are weaned and protective maternally derived antibodies start to decline.

To protect against PCV2 infection and its associated signs of disease, several commercial vaccines are available, and these are being used worldwide in very large numbers. Different types of PCV2 vaccines are for example: a vaccine based on inactivated whole PCV2 virus (Circovac™ Merial), or on inactivated chimeric PCV1/PCV2 virus (Suvaxyn™ PCV, Fostera™ PCV, Zoetis). Most common however is a subunit vaccine based on recombinant expressed PCV2 capsid protein, commonly named: ORF2 protein (Ingelvac™ CircoFLEX, Boehringer Ingelheim; and: Circumvent™ PCV, Porcilis™ PCV, MSD AH). The ORF2 protein subunit vaccine is commonly produced by the expression of the PCV2 ORF2 gene in a recombinant expression system; most used is the baculovirus-insect cell expression system. The expressed ORF2 protein self-assembles into virus-like particles (VLP), which resemble a native PCV2 virion, except that it lacks the viral genome content, and therefore is non-replicative. Vaccines based on such PCV2 ORF2 VLPs are very stable, are highly immunogenic when formulated with an adjuvant, and have demonstrated to be safe for pigs of all ages, whether seropositive for PCV2 antibodies or not. A typical full dose of vaccine based on PCV2 ORF2 protein contains about 80 µg of ORF2 protein, in a dose volume of 2 ml/animal. However these subunit vaccines are efficacious already at about 20 microgram ORF2 per animal dose, see EP 1.926.496. Also they can be given as a single shot vaccine, and they can be given by different routes of administration, such as intramuscular (IM), subcutaneous (SC), or intradermal (ID).

Within the species PCV2 there are different genotypes of the virus. These can be distinguished by way of the genetic distance between their ORF2 genes, and a variety of naming conventions have been used in the past. However, Segales et al. (2008, Vet. Rec., vol. 162, p. 867-868) published a method that has become the standard currently adhered to for determining and naming PCV2 genotypes. Of the 5 different genotypes of PCV2 that are now recognised, only three are currently of veterinary relevance in the field: PCV2a, PCV2b, and PCV2d.

While all commercial PCV2 vaccines are currently based on PCV2a, the genotypes PCV2b and 2d seem to be increasing in prevalence in the field. For a review see: Karuppannan & Opriessnig, 2017, Viruses, vol. 9, p. 9, doi: 10.3390/v9050099. Although these authors conclude there is an adequate level of cross-protection between these genotypes, it is generally preferred to apply type-homologous vaccines. Consequently, there is a need in the field to produce safe, cheap and effective vaccines also for PCV2 genotypes other than PCV2a.

WO 2009/000459 (University Gent) describes diagnostics for identifying antigenic- or pathogenic variants of PCV2, based on the ORF2 protein; specifically methods and antibodies useful for that purpose. Nucleic acid and amino acid sequences are described of ORF2 from two PCV2b strains. Several mutations of ORF2 protein are suggested, in order to change the profile of recognition by monoclonal antibodies. Among the many suggested mutations, one is that of Threonine at amino acid position 131 to Proline. However, WO 2009/000459 only sufficiently discloses the serologic testing of unmutated (wildtype) strains of PCV2a (Stoon 1010, 1121) and PCV2b (48285), and only discloses the expression of unmutated ORF2 from one of the wildtype PCV2a strains (Stoon 1010) in insect cells.

Subsequently Saha et al., 2012 (J. of Gen. Virol., vol. 93, p. 1548-1555), describe among others the expression of PCV2a ORF2 protein with T131P mutation in PK-15 cells, by the transfection of infectious clones of the mutated PCV2 genome.

WO 2010/068969 (Vectogen) describes methods of vaccination against PCV2 by viral-vector delivery of ORF2, whereby the ORF2 protein has been mutated by replacing or removing the 'nuclear localisation signal', i.e. the N-terminal 41 amino acids of ORF2. As a result ORF2 then becomes expressed in the cytoplasm or is secreted from vector-infected cells. Preferred viral vector is porcine Adenovirus.

WO 2015/051099 (Boehringer-Ingelheim) describes methods for increasing the expression level of PCV2b ORF2 protein and its virus-like particles in a baculovirus-insect cell expression system, by introducing a mutation in the PCV2b ORF2 coding sequence: the mutation disclosed is a substitution of Arginine at amino acid position 63, preferably to Threonine. There is no mention of any mutation at amino acid position 131 of PCV2b ORF2, and no information on any problems with the expression of this protein in insect cells.

EP 17184630 (Intervet Int. BV) discloses that in a PCV2 vaccine, ORF2 protein of the PCV2b genotype was found to provide not only homologous protection, but also good cross-protection against heterologous genotypes PCV2a and PCV2d. Also this effect was—unexpectedly—obtained even in very low amounts, of less than 20 µg PCV2b ORF2 protein per animal dose. Consequently it will suffice to vaccinate swine with a low dose of PCV2b ORF2 protein, to provide effective immunoprotection against all current strains of PCV2.

The use of insect cells for the recombinant expression of protein is well known, and is applied in different ways: expression in live insects, in primary insect cells, or in immortalised insect cell-lines in culture. Most used insect cells are of Lepidopteran origin such as from the *Spodoptera* or *Trichoplusia* genera. The use of these cells is often in the context of the popular baculovirus-insect cell expression system, wherein a recombinant baculovirus is used to infect Lepidopteran cells in culture. A baculovirus contains a number of strong promoters which are not required when the virus replicates in cell-culture; these can then be used to drive the expression of a heterologous gene.

It is an object of the present invention to overcome a disadvantage in the prior art, and to accommodate to a need in the field, by providing a way to optimise the recombinant expression of PCV2 ORF2 protein in insect cells.

When investigating the preparation of PCV2 vaccines based on ORF2 protein subunits, the inventors discovered that the recombinant expression of ORF2 protein from PCV2b genotype viral strains, in insect cells, was not as straightforward as for ORF2 protein of the PCV2a genotype. The expressed PCV2b ORF2 protein was found to have a natural tendency to accumulate at the nucleus of the insect cells in which it was expressed. In this form, total expression levels of the PCV2b ORF2 protein were much reduced, and the protein proved to be very difficult to harvest and to purify by downstream processing; even when aggressive dissociation was used, only very low amounts of ORF2 protein could be isolated. Also, in the small amounts of protein that could be isolated, the amount of VLPs was very low; apparently the nuclear localisation prevented the ORF2 protein to self-assemble into VLPs to a significant degree. As a result the immunogenicity of this expressed protein was much reduced.

Surprisingly it was found that when a very specific amino acid substitution was introduced into the ORF2 protein of PCV2b, the nuclear accumulation upon expression in insect cells could be largely prevented.

The specific amino acid substitution involved the change of the amino acid naturally occurring at position 131 of the full length PCV2b ORF2 protein, into a Proline amino acid. With a Proline at position 131 most of the expressed mutant PCV2b ORF2 protein ("ORF2b-131P") then occurred in the insect cell's cytoplasm, instead of accumulating at the nucleus. This was found to increase total levels of expression, as well as greatly facilitate the harvesting of the mutant PCV2b ORF2 protein from these insect cells; in this cytoplasmic state, low-impact, standard isolation procedures could be used, so that high amounts of the protein could be easily be isolated. Also, most of the ORF2b-131P was found to have effectively assembled into VLP's, which are very effective in a PCV2 vaccine for porcine animals.

This was unexpected, especially when compared to the situation with PCV2a ORF2 protein: while in ORF2 protein from PCV2b virus the natural amino acid at position 131 is typically a Threonine; in PCV2a viruses some have a Threonine at 131, and some have a Proline. However when expressed in insect cells, neither of the two variants of PCV2a ORF2 accumulates at the nucleus. Consequently there was no indication to suspect that this particular amino acid position would be the cause of the nuclear accumulation observed for PCV2b ORF2 protein when expressed in insect cells.

Even more remarkable was that PCV2d ORF2 protein, which also shows nuclear accumulation upon expression in insect cells, could not be reversed to a cytoplasmic expression pattern after substitution of its natural Threonine at position 131 to Proline.

Apparently the situation around expression of PCV2 ORF2 protein in insect cells is unique for each of the genotypes.

It is not known how the amino acid substitution to 131P prevents the accumulation of PCV2b ORF2 protein at the nucleus, upon expression in insect cells. Although the inventors do not want to be bound by any theory or model that might explain these findings, they speculate that having a Proline amino acid at this particular position in the ORF2 protein of the PCV2b genotype, induces a change in the properties of this ORF2 protein. The change may for instance affect the 3-dimensional folding or the hydrophobicity profile of the ORF2 protein, which may affect its routing inside the insect cell.

This discovery opens the way to a number of advantageous uses, by improving the availability and the antigenic quality of recombinant-expressed PCV2b ORF2 protein. In turn this allows the convenient manufacture at large scale of effective PCV2 subunit vaccines for porcine animals; because no aggressive dissociative compounds or complicated techniques are required for its isolation, the expressed protein can be produced in a cheap, safe, and efficient way.

In this way one or more objects of the present invention can be met, and consequently one or more disadvantages of the prior art can be overcome.

Therefore in one aspect the invention relates to insect cells comprising a heterologous nucleic acid comprising:
a. a nucleotide sequence encoding an ORF2 protein from porcine circovirus 2 of genotype 2b (PCV2b), and
b. a transcription control sequence that is operatively linked to said nucleotide sequence, characterised in that the nucleotide sequence encodes a mutant PCV2b ORF2 protein having a Proline at amino acid position number 131.

For the invention, the "insect cells" are cells derived from an organism of the class Insecta. The cells are viable (i.e. capable of replicating) and sufficiently intact to be capable of protein expression. The cells may be resting or active, and may be in any stage of the cell cycle. The insect cells can be employed for the invention in different ways: either by using a whole insect; by using an extract or part of an insect; by using primary cells derived from an insect; using an insect's tissue or organ; or by using an immortalised insect cell-line.

The insect cells of the invention will normally be contained in a suitable carrier. Such a carrier is a composition that maintains the viability of the insect cells, and is for example a liquid, such as a buffered solution or a culture medium. In the context of the use of whole insects, the body of the insect organism itself functions as the carrier.

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Thus any such text section, paragraph, claim, etc., can therefore also relate to one or more embodiment(s) wherein the term "comprising" (or its variants) is replaced by terms such as "consist of", "consisting of", or "consist essentially of".

For the invention, a nucleic acid is "heterologous" to the insect cells that comprise it, if the nucleic acid was not present in the nucleic acids of the parental insect cells from which the cells were derived. The nucleic acid can be of any type, e.g. DNA or RNA.

The heterologous nucleic acid for the invention can be introduced into the insect cells according to the invention in different ways, such as by transfection or electroporation of the nucleic acid, possibly on a carrier; alternatively by infection by a recombinant micro-organism, for example a virus.

A nucleotide sequence "is encoding", or the similar "encodes", a protein when its transcription and/or translation results in that protein being expressed. Typically such a nucleotide sequence capable of encoding a protein is called an open reading frame (ORF), indicating that no undesired stop codons are present that would prematurely terminate the translation of the protein. Such a nucleotide sequence may be a gene encoding a complete protein, or may be a gene-fragment, encoding a section of a protein, for example encoding only the mature or the secreted form of a protein, i.e. without a 'leader', 'anchor', or 'signal sequence'. The nucleotide sequence may be of natural or of synthetic origin.

For the invention, a "protein" is a molecular chain of amino acids. A protein can be a native or a mature protein, a pre- or pro-protein, or a part of a protein. Inter alia: peptides, oligopeptides and polypeptides are included within the definition of protein.

"ORF2" protein for the invention refers to a protein encoded by open reading frame 2 (ORF2) on the genome of PCV, or by a part of ORF2. The full length PCV2 ORF2 protein is commonly 233 amino acids in length, and when tested in SDS-polyacrylamide gel electrophoresis (SDS-PAGE) displays a relative molecular weight of about 26 kDa. However truncated forms of the ORF2 protein are well-known and may advantageously be used for the invention, for example the truncated form of the PCV2 ORF2 protein that is missing 30 amino acid from its N-terminal side. The ORF2 protein is also called the capsid, and the encoding nucleic acid sequence is called the ORF2 gene, or the capsid gene.

Computer-programs that can assist with the analysis of coding regions, and represent such information in convenient ways are available commercially from a variety of suppliers.

"Porcine circovirus 2" or PCV2 refers to the circovirus of that species, having the characterising features of its taxonomic group-members such as the morphologic, genomic, and biochemical characteristics, as well as the biological characteristics such as physiologic, immunologic, or pathologic behaviour.

As is known in the field, the classification of a micro-organism as a particular species is based on a combination of such features. The invention therefore also includes PCV2 that are sub-classified therefrom in any way, for instance as a subspecies, strain, isolate, genotype, variant, subtype or subgroup and the like.

It will be apparent to a person skilled in the field of the invention that while a particular PCV2 for the invention may currently be assigned to that species, however that is a taxonomic classification that could change in time as new insights can lead to reclassification into a new or different taxonomic group. However, as this does not change the micro-organism itself, or its antigenic repertoire, but only it's scientific name or classification, such re-classified micro-organisms remain within the scope of the invention.

PCV2 for use in the invention can be obtained from a variety of sources, e.g. as field isolate from a porcine in the wild or on a farm, or from various laboratories, (depository) institutions, or (veterinary) universities. Alternatively a PCV2 can be reconstituted from digital sequence information, by synthesizing its genomic nucleic acid and transfecting that into appropriate cells.

Genotyping of PCV2 is done by comparing nucleotide sequences. For the invention a "PCV2 of genotype 2b", or a "PCV2b", is a PCV2 virus that is classified in genotype group b using the method of Segales et al. (2008, Vet. rec. vol. 162, p. 867-868). This method applies PCV2 genotyping based on the P-distance between PCV2 ORF2 genes, i.e. the ratio of nucleotides that differ between two PCV2 ORF2 genes, per total number of nucleotides of their PCV2 ORF2 gene. The cut-off for the different genotypes of PCV2 identified by Segales et al. is at an ORF2 P-distance of 0.035; so when the P difference is smaller, then the two sequences belong to the same genotype.

For the invention, the reference virus of a PCV2 of genotype 2b is isolate 'Imp.1011', also known as strain 48285, for which the genome sequence is published in GenBank™ under accession number: AF055394.

Consequently any PCV2 virus having an ORF2 gene P-distance of less than 0.035 with the ORF2 gene of strain 48285, calculated using the method of Segales et al. (supra), is a PCV2b virus for the invention.

However, and as the skilled person will appreciate, because the genome of PCV is single stranded and circular, the coding region of the ORF2 gene may not be immediate apparent from a particular linear nucleotide sequence, and may require the nucleotide sequence to be inversed, complemented, and/or rotated. For example: in the genomic sequence of PCV2b strain 48285 in GenBank accession number: AF055394, the ORF2 gene runs on the linear published strand from nucleotide number 314 to nt. 1 and continues from nt. 1767 up to and including nt. 1383; together this represents the 699 nucleotides of the ORF2 gene (not including the stop codon), and is encoded by the strand complementary to this region of the published strand. Again, such analysis and representation of coding regions can conveniently be performed using a commercially available computer-program.

A similar approach applies for "PCV2 genotype 2a" (PCV2a), and "PCV2 genotype 2d" (PCV2d), as used herein; the reference virus for PCV2a is isolate 'Imp.1010', a.k.a. 'Stoon 1010', accession number: AF055392; and the reference virus for PCV2d is isolate 'S99-1542/3a', acc.nr.: JX512856.

Methods to identify a virus as a PCV2 virus, to determine the nucleotide sequence of its ORF2 gene, and to calculate a P-distance compared to the ORF2 gene of strain 48285 are well-known and readily available to the person skilled in the art of the present invention.

A "transcription control sequence" is a functional region of nucleic acid, typically in DNA, which through the binding of control factors, induces the protein-expression machinery of a cell to initiate and perform the transcription of DNA into RNA of a downstream coding region. Such a transcription control region (TCR), may also be called a promoter, and commonly contains a number of regulatory regions such as the 'transcription start site', located at about 30-40 nucleotides upstream of the first start codon. Other well-known conserved elements are the TATA box, the CAAT box, and the GC box. The TCR may also comprise a so-called enhancer which is involved in binding regulatory factors that can influence the time, the duration, the conditions, and the level of transcription.

Consequently, the transcription (and subsequent translation) may be of a temporary or of a permanent nature, i.e. be transient or stable expression, depending on details of the TCR used and of the genetic construct as a whole.

A TCR for the expression of a (heterologous) gene needs to be able to effectively drive the transcription of that downstream coding region. This is commonly referred to as the TCR being "operatively linked" to a gene, such that the gene is 'under the control' of, or is 'driven by' the TCR. This commonly means that the TCR and the coding region are connected on the same molecule, in effective proximity, and with no signals or sequences between them that would intervene with an effective transcription.

The terms "mutant PCV2b ORF2 protein", serve to indicate that the expressed PCV2b ORF2 protein is not identical to the wildtype version of that protein, but comprises a mutation. Such mutation can be introduced in different ways, using in vivo or in vitro techniques. Most effective is however the use of recombinant DNA technology to subclone a PCV2b ORF2 gene in a bacterial plasmid and employ for example the polymerase chain reaction (PCR) and synthetic primers to introduce a desired mutation at a desired location. Details are presented in the Examples hereinafter. In this way for example the DNA sequence of the parental PCV2b ORF2 gene, from GenBank acc. nr. AF055394 was manipulated whereby the wildtype nucleotide triplet encoding Threonine at amino acid position 131: 5'-aca-3', was mutated to the triplet: 5'-ccc-3', encoding Proline.

Further manipulation can be applied by codon-optimisation of the ORF2 gene, to make it better comply with the coding preference of insect cells and/or of a baculovirus. For example using the codon preference of the polyhedrin gene from AcMNPV baculovirus as published in: Hooft van Iddekinge et al., 1983, Virology, vol. 131, p. 561-565. The concept of codon-optimisation of a gene for heterologous expression is well-known; typically such mutations are all silent, meaning that while this changes the encoding nucleotide sequence, it does not change the amino acid sequence of the encoded protein. Details are provided in the Examples.

Codon-optimisation was found to increase the level of expression of ORF2 protein in insect cells. To a minimal degree this also changed the nuclear localisation of wildtype PCV2b ORF2 protein when expressed in insect cells. However a substantial prevention of nuclear accumulation in insect cells could only be obtained for ORF2 protein from PCV2b by the substitution of the amino acid at position 131 by Proline.

For the invention, 'wildtype' refers to the form of a (micro-)organism in which it occurs in its natural form in the wild, for example: the form of the parental organism before it was changed by human intervention.

The generation, construction and assembly of the heterologous nucleic acid expressing the mutant PCV2b ORF2 protein for the invention, can be done by well-known molecular biological techniques, involving cloning, transfection, recombination, selection, and amplification. These, and other techniques are explained in great detail in standard text-books like Sambrook & Russell: "Molecular cloning: a laboratory manual" (2001, Cold Spring Harbour Laboratory Press; ISBN: 0879695773); Ausubel et al., in: Current Protocols in Molecular Biology (J. Wiley and Sons Inc., NY, 2003, ISBN: 047150338X); C. Dieffenbach & G. Dveksler: "PCR primers: a laboratory manual" (CSHL Press, ISBN 0879696540); and "PCR protocols", by: J. Bartlett and D. Stirling (Humana press, ISBN: 0896036421).

For the invention a particular "amino acid position" is numbered on the basis of the numbering of the amino acids in the amino acid sequence of the full length ORF2 protein from the reference strain for that PCV2 genotype. For PCV2b the reference strain is 48285, and the full length amino acid sequence of its ORF2 protein is published in GenBank under accession number AAC35331.

The insect cells according to the invention can express ORF2b-131P; the mutant PCV2b ORF2 protein (for the most part) no longer accumulates at the nucleus, but is dispersed throughout the insect cell's cytoplasm. This difference in the cellular location of the mutant PCV2b ORF2 protein, as compared to its unmutated counterpart, can be readily detected, among others by (light-)microscopy and visualisation using immuno-fluorescence technology. Details are presented in the Examples section.

The residual level of nuclear accumulation of the ORF2b-131P protein was found to differ somewhat depending on the genetic construct used to express the mutant PCV2b ORF2 protein in insect cells: expression via recombinant baculovirus made using the Bac-to-Bac system, still showed some nuclear accumulation, e.g. about 10% of the level observed for the wildtype PCV2b ORF2 protein. However when the mutant protein was produced from a recombinant baculovirus constructed via the ProEasy system, no detectable nuclear accumulation was observed anymore. In addition the level of protein expression was higher than that produced by Bac-to-Bac recombinant baculovirus.

This can probably be explained from the constitution of the genetic construct used: recombinant baculoviruses prepared from Bac-to-Bac constructs, still carry elements from the expression cassette of the transfervector in their genome, such as a transposon and an antibiotic resistance gene. These may influence the level of replication and expression. However ProEasy recombinants no longer carry such additional genetic elements.

Details of preferred embodiments and other aspects of the invention will be described below.

In an embodiment, the nucleotide sequence encoding the mutant PCV2b Orf2 protein has been codon optimised. More preferably: has been codon optimised to match the codon preference of the polyhedrin gene of AcMNPV baculovirus.

Most preferred, the nucleotide sequence encoding the mutant PCV2b Orf2 protein is SEQ ID NO: 1. This represents the ORF2 sequence of PCV2b strain 48285, wherein the triplet encoding amino acid position number 131 has been mutated to 5'-ccc-3', encoding Proline. In addition the codon usage has been adapted to fit the codon preference of the AcMNPV polyhedrin gene. SEQ ID NO: 2 in turn lists the ORF2b-131P protein sequence that is encoded by SEQ ID NO: 1.

As a consequence of the mutations applied to the PCV2b ORF2 gene, in particular because of the codon-optimisation, the nucleotide sequence identity between SEQ ID NO: 1 and the corresponding region of AF055394, the wildtype ORF2b gene, is 77.2%. However, because the codon-optimising mutations are silent, the amino-acid sequence identity between SEQ ID NO: 2 and AAC35331 (which is the amino acid sequence of the wild type PCV2b ORF2 protein from strain 48285) is 99.6%, namely only differing in the amino acid at position 131.

The use of cells from a variety of insects is well-known. Several of these can also be used in the context of the baculovirus-insect cell expression system, as they can be infected with a baculovirus. See for example: Chen et al., 2005, In vitro Cell. Dev. Biol. Anim., vol. 41, p. 43-49.

Therefore in an embodiment the insect cells according to the invention are derived from an insect selected from the group consisting of: *Autographa californica* (alfalfa looper), *Spodoptera frugiperda* (fall army worm), *Spodoptera exigua* (beet armyworm), *Trichoplusia ni* (cabbage looper), *Lymantria dispar* (gypsy moth), *Bombyx mori* (silkworm), *Anticarsia gemmatalis* (velvetbean caterpillar), *Heliothis virescens* (tobacco budworm), *Heliothis subflexa* (Subflexus straw moth), *Mamestra brassicae* (cabbage moth), *Helicoverpa armigera* (cotton bollworm), *Helicoverpa zea* (corn earworm), *Agrotis ipsilon* (black cutworm), *Anagrapha falcifera* (celery looper), *Galleria mellonella* (honeycomb moth), *Rachiplusia ou* (gray looper), *Plutella xylostella* (diamondback moth), *Drosophila melanogaster* (fruit fly), and *Aedes aegypti* (mosquito).

In an embodiment, the insect cells according to the invention are derived from an insect from the order Lepidoptera; more preferred from the family of the Noctuidae; even more preferred from one of the genera: *Spodoptera* or *Trichoplusia.*

In an embodiment the insect cells according to the invention are derived from an insect of the species *Spodoptera frugiperda.*

In an embodiment the insect cells according to the invention are derived from an insect of the species *Trichoplusia ni.*

It is known and feasible to breed complete insects for heterologous protein expression, and in this way apply the insect cells according to the invention. However it will be more convenient to utilise insect cells in the form of an immortalised insect cell-line, as this will allow more flexible production and scale-up under controlled conditions. Such established insect cell-lines can then be used to construct insect cells according to the invention, using routine methods as described herein.

Well-known insect cell-lines that are suitable for such use are: Sf9 and Sf21, both derived from *S. frugiperda*; High Five™ (Hi-5), derived from *T. ni*; Bm5, derived from *B. mori*; and Ld652Y and LdElta, derived from *L. dispar.*

Therefore in an embodiment, the insect cells according to the invention are prepared from cells of an insect cell-line selected from the group consisting of Sf9, Sf21, Hi-5, Bm5, Ld652Y and LdElta, or a cell-line derived from one of these.

Preferably the insect cells according to the invention are prepared from an insect cell-line of Sf9 or Sf21.

Procedures, equipment, and materials for the culturing of insect cell-lines are well-known, and can be applied at any desired scale, e.g. from 5 ml up to 5000 litres. In particular specialised insect cell culture media are available, for example: Sf-900™ (Thermo Fisher Scientific); Ex-Cell™ 400 series (Sigma Aldrich); and Insect-XPRESS™ (Lonza).

Dependent on the characteristics of these media, they either need the addition of a certain percentage of serum, such as foetal calf serum, or can be used serum-free. Further additives may be added, such as Glutamine, antibiotics, anti-foaming agent, etc.

There are several ways in which an insect cell according to the invention can comprise a heterologous nucleic acid for the invention, one example is by stable integration in the genome of the insect cell. Ways to achieve genomic integration are e.g.: by random insertions such as by transposon technology, or by directed insertions using for example homologous recombination or CRISPR-Cas technology.

Alternatively, insect cells can be transfected by chemical (e.g. Lipofectin™) or physical (e.g. electroporation) means with a heterologous nucleic acid, which itself may be on a carrier such as a plasmid. The heterologous nucleic acid can be transiently or stably expressed by the insect cell.

However the preferred way to introduce such a heterologous nucleic acid into insect cells according to the invention, is by the use of a recombinant baculovirus. Such a baculovirus will for example contain a heterologous gene of interest stably integrated in its viral genome, and operatively linked to a strong baculovirus promoter, such as the promoters of the very late genes p10 or polyhedrin.

Therefore in an embodiment of the insect cells according to the invention, the transcription control sequence is a baculovirus p10 gene promoter or a baculovirus polyhedrin gene promoter.

Next the recombinant baculovirus is made to enter the insect cell; this can be done passively for example by transfection of the genome of the recombinant baculovirus, or actively by the infection of a susceptible insect cell by an infective recombinant baculovirus. The insect cell, by comprising the recombinant baculovirus or its genome inside it, will then also comprise the heterologous nucleic acid for the invention. For the invention "inside the cell" simply refers to the location of the recombinant baculovirus genome, being at the internal side of the insect cell's cellular membrane, e.g. in the cytoplasm.

Inside the insect cell, the recombinant baculovirus or its genome will be replicated, leading to the expression of the heterologous gene in the insect cell. The heterologous expression product can then be harvested, either from the insect cells or from the cell's environment such as the cell's culture medium.

Therefore in an embodiment of the insect cells according to the invention, the heterologous nucleic acid is comprised in a recombinant baculovirus genome.

A "baculovirus" is a member of the family Baculoviridae; preferably a member of the genus Alphabaculovirus.

A baculovirus for the invention is "recombinant" if it has been altered by human intervention as compared to its wildtype form, in order to comprise a heterologous nucleic acid. Preferably such recombinant baculovirus is created by methods of genetic manipulation.

As the skilled person will appreciate when considering the insect cells according to the invention in a particular culture vessel, or in a well of a culture plate, the number of the cells that is actually comprising the heterologous nucleic acid for the invention will be dynamic. This is because of a number of biological reasons such as the cell's lifecycle status or the level of infection or transfection. While it is preferred to have as many cells as possible comprising and expressing the heterologous nucleic acid, it is not necessary that at a certain point in time, each and every individual insect cell of that group comprises the heterologous nucleic acid.

The combined use of insect cells and recombinant baculovirus, for the expression of a heterologous protein, is commonly referred to as the 'baculovirus-insect cell expression system'. Examples of papers, text-books, and reviews on this system are: Luckow et al., 1988, Bio-technology, vol. 6, p. 47; Baculovirus Expression Vectors: A Laboratory Manual by David R. O'Reilly, Oxford University press, 1993, ISBN: 0716770172; The Baculovirus Expression System: A laboratory guide, ed. King & Possee, 1992, ISBN: 9401050473; and a review is: van Oers et al., 2015, J. of Gen. Virology, vol. 96, p. 6-23.

Efficient expression using the baculovirus-insect cell expression system can be applied from the lab-scale up to very large industrial scale production. Heterologous genes of varied origin have been expressed in the 30 years that the baculovirus-insect cell expression system has been known, and many tools are commercially available for applying this technology.

Several baculovirus species have been used as convenient vectors for expression of heterologous proteins in insect cells. Examples of baculoviruses used in the baculovirus-insect cell expression system are (multicapsid) nucleopolyhedroviruses of *Autographa californica* (alfalfa looper): AcMNPV, or of *Bombyx mori*: BmNPV.

In an embodiment of the recombinant baculovirus comprising the heterologous nucleic acid for the invention, said baculovirus is an AcMNPV or a BmNPV.

Many tools and kits are available commercially to efficiently generate and select recombinant baculoviruses for use in the invention. For example: Bac-to-Bac™ (Thermo Fisher Sci., Waltham, Mass., USA); ProEasy™ (AB Vector, San Diego, Calif., USA); and flashBAC™ (Oxford Expression Technologies, Oxford, UK).

To optimise the replication- and protein expression levels, the recombinant baculovirus comprising the heterologous nucleic acid for the invention, is preferably as close as possible to a wildtype baculovirus, except of course for the insertion of the heterologous nucleic acid, and the subsequent disruption or deletion at the insertion locus. In practice that means the recombinant baculovirus preferably does not contain further genetic elements from the recombination process in its genome, for example elements such as: a tag, label, marker-gene, transposon element, antibiotic resistance gene, etc.

Therefore in an embodiment the recombinant baculovirus comprising the heterologous nucleic acid for the invention does not contain further genetic elements from the recombination process in its genome.

In a preferred embodiment the recombinant baculovirus does not comprise an antibiotic resistance gene from the transfervector that was used for the construction of that recombinant baculovirus.

In an embodiment of the insect cells according to the invention, one, more, or all of the conditions apply, selected from the group consisting of:

the nucleotide sequence encoding the mutant PCV2b Orf2 protein has been codon-optimised; more preferably: has been codon optimised to match the codon preference of the polyhedrin gene of AcMNPV baculovirus;
the nucleotide sequence encoding the mutant PCV2b ORF2 protein is SEQ ID NO: 1;
the insect cells according to the invention are derived from an insect from the order Lepidoptera; more preferred from the family of the Noctuidae; even more preferred from one of the genera: *Spodoptera* or *Trichoplusia*;
the insect cells according to the invention are derived from an insect of the species *Spodoptera frugiperda*;
the insect cells according to the invention are derived from an insect of the species *Trichoplusia ni*;
the insect cells according to the invention are prepared from cells of an insect cell-line selected from the group consisting of Sf9, Sf21, Hi-5, Bm5, Ld652Y and LdElta, or a cell-line derived from one of these.
the insect cells according to the invention are prepared from an insect cell-line of Sf9 or Sf21.
the transcription control sequence is a baculovirus p10 gene promoter or a baculovirus polyhedrin gene promoter;
the heterologous nucleic acid is comprised in a recombinant baculovirus genome that is inside the insect cell;
the recombinant baculovirus comprising the heterologous nucleic acid for the invention is an AcMNPV or a BmNPV; and
the recombinant baculovirus comprising the heterologous nucleic acid for the invention does not contain further genetic elements from the recombination process in its genome.

As described herein, the mutation to PCV2b ORF2 protein as described for the invention, allows an increased expression of the ORF2b-131P protein from the insect cells according to the invention. Especially, this allows the generation of VLPs comprising PCV2b ORF2 protein to much a greater extent as is possible without this mutation.

Therefore in a further aspect the invention relates to virus-like particles (VLPs) of a mutant PCV2b ORF2 protein, characterised in that the mutant PCV2b ORF2 protein has a Proline at amino acid position number 131.

Materials and methods for characterising and using VLPs of ORF2b-131P protein are well-known in the art.

Preferably the expression of the mutant PCV2b ORF2 protein for the invention in insect cells is achieved by the use of the baculovirus-insect cell expression system, as described above.

Therefore in a further aspect the invention relates to a method for the expression of a mutant PCV2b ORF2 protein in the insect cells according to the invention, the method employing the use of the baculovirus-insect cell expression system.

In particular when the insect cells according to the invention that are used for the expression of the mutant PCV2b ORF2 protein for the invention are cells of an insect cell-line, they can conveniently be cultured using standard cell-culturing equipment, which results in the expression of the mutant PCV2b ORF2 protein. Insect cell-culturing equipment is available at any scale; from a simple T-flask or a spinner flask placed in an incubation cabinet at the appropriate temperature; all the way up to a large-scale industrial fermenter with heated mantle, stirrer, and sparger, with automated control of process parameters such as temperature, pH and dissolved oxygen.

Subsequent to the culturing of the insect cells according to the invention, the expressed mutant PCV2b ORF2 protein is harvested from the insect cell culture for further use. Like the culturing, such harvesting can be done using standard procedures well-known in the art. Also, when required the culture can first be inactivated (i.e. sterilised) by physical (e.g. heat, irradiation) or chemical (e.g. Bromo-ethylene-imine (BEI)) means.

Dependent on the characteristics of the insect cell used, and the type of the expression applied, the expressed mutant PCV2b ORF2 protein accumulates inside the insect cells, or at its membrane, or is secreted out of the cell. Even when not actively secreted, the protein may end up to some extent in the cell's culture medium when cells rupture.

A method of harvesting the expressed protein can then be selected:

When the expressed protein is primarily present in the culture medium, this can be harvested, for example as the supernatant after centrifugation of the culture. The bulk of the culture volume can then be reduced to a desired degree, for example using concentration, conveniently by some method of ultrafiltration, all well-known in the art.

When the protein is mainly in the cells, these can be isolated from the bulk of the culture volume for example by centrifugation of the culture, and resuspending the cell-pellet in a smaller volume. Next the cells can be disrupted using more or less invasive techniques.

Next the expressed protein can be obtained using some method of extraction and/or purification.

All this can be performed by the skilled person using nothing but well-known methods and materials.

Therefore, in a further aspect, the invention relates to a method for the production of a mutant PCV2b ORF2 protein having a Proline at amino acid position number 131, the production comprising one or both steps selected from:
  culturing of the insect cells according to the invention; and
  harvesting of the mutant PCV2b ORF2 protein from the insect cell culture.

Especially advantageous result of the invention is that the mutant PCV2b ORF2 protein no longer accumulates at the nucleus of the insect cells in which it is expressed. Not only did this increase the total level of expression, but it also greatly facilitated the harvesting of the mutant PCV2b ORF2 protein from these insect cells. That is because in this cytoplasmic state, very low-impact, and standard isolation procedures could be used, yielding relatively large amounts of the mutant PCV2b ORF2 protein. In addition the harvested protein was of excellent immunological quality as most of the ORF2b-131P was found to have effectively assembled into VLP's.

More specifically: the harvesting of unmutated PCV2b ORF2 protein in substantive amounts would require extraction by using chemicals such as detergents or chaotropic agents, e.g. SDS, Urea, deoxycholate, or guanidine-HCl, etcetera. Subsequently these would need to be removed again. The use of such aggressive chemicals at large scale is of course not desirable.

However, the harvesting of the mutant PCV2b ORF2 protein can be achieved by safe, convenient, and very mild techniques without the use of chemicals, by applying for example sonication or freeze-thawing of the insect cells.

Therefore in an embodiment of the method for the production of mutant PCV2b ORF2 protein according to the invention, the step of harvesting the mutant PCV2b ORF2 protein from the insect cell culture does not employ a detergent or a chaotropic agent.

In an embodiment the harvesting employs a physical- and not a chemical method for the lysis of the insect cells; examples of a physical method of cell-lysis are: sonication, freeze-thawing, and French press.

For the invention, a 'culture' of insect cells, or the similar 'culturing', refers to the incubation of insect cells under appropriate conditions, allowing the cells to grow and divide, and express the heterologous insert.

Such culturing of insect cells will typically involve the use of appropriate cell-culture medium and convenient equipment; all are well-known in the art and commercially available. For example cultures of cell-lines from insects of the *Spodoptera* or *Trichoplusia* genera are commonly cultured under aerobic conditions, in monolayer or in suspension, at 26-28° C.

Under practical conditions it will be convenient to have a separate culture vessel for the generation of clean insect cells, kept well clear from equipment used for the culturing of insect cells to be infected or transfected. Commonly the insect cells are prepared as master cell-stock and working cell-stock. This approach allows the level of quality control that is required for the preparation of recombinant proteins for pharmaceutical use.

In an embodiment of the method for the production of mutant PCV2b ORF2 protein according to the invention, the produced protein is in the form of VLPs.

By applying the methods for preparation of mutant PCV2b ORF2 protein according to the invention, the mutant PCV2b ORF2 protein can be prepared in sufficient quantities and with the required immunological efficacy, to manufacture a vaccine against PCV2 or associated signs of disease.

Therefore, in a further aspect the invention relates to a vaccine for porcine animals for reduction of infection by PCV2 or of associated signs of disease, the vaccine comprising a mutant PCV2b ORF2 protein in a pharmaceutically acceptable carrier, characterised in that said mutant PCV2b ORF2 protein has a Proline at amino acid position number 131.

In an embodiment the vaccine according to the invention is for reduction of infection by PCV2 of genotype 2a, 2b, and/or 2d.

More preferred the vaccine is for reduction of infection by PCV2b.

A "vaccine" is well known to be a composition comprising an immunologically active compound, in a pharmaceutically acceptable carrier. The 'immunologically active compound'-when in the form of an 'antigen'—will be recognised by the immune system of the inoculated target inducing an immunological response. The response may originate from the innate or from the acquired immune system, and may be of the cellular and/or of the humoral type.

For the invention "porcine" refers to animals of the family of Suidae, and preferably to animals of the genus *Sus*, for example: a wild or a domestic pig, wild boar, babirusa, or warthog. This also includes porcines indicated by an arbitrary name referring to their sex or age such as: sow, boar, hog, gilt, weaner, or piglet.

The vaccine according to the invention can provide for a "reduction of infection by PCV2", which refers to preventing or reducing the establishment or the proliferation of a productive infection by PCV2 in a target animal. This is achieved for example by reducing the viral load or shortening the duration of the viral replication. In turn this leads in the target animal to a reduction of the number, the intensity, or the severity of lesions and consequential clinical signs of disease caused by the viral infection. Such a vaccine is colloquially referred to as a: vaccine 'against' PCV2, or a 'PCV2 vaccine'.

In a preferred embodiment the vaccine according to the invention works as an aid in the prevention of PCV2 viremia, and/or as an aid in the prevention of the shedding of PCV2 by infected animals.

In addition to vaccine efficacy against infection by PCV2, the vaccine according to the invention can also provide a "reduction . . . of associated signs of disease" which refers to porcine circovirus associated disease (PCVAD) that may occur as secondary or concurrent disease. Like for PCV2, the vaccine according to the invention can provide a reduction of the severity and/or the duration of the symptoms or consequences of such PCVAD.

PCV2 vaccines reduce PCV2 viral replication and -spread. This reduces PCV2 viral load in blood, lung, and lymphoid tissues (e.g. tonsils, spleen, and lymph nodes), and protects against lymphoid depletion, spread of infections, and against PCV2 associated diseases. Consequently this restores general health and performance in herds of vaccinated porcines as is reflected in one or more of the parameters: reduced mortality, better average daily weight gain, improved feed conversion, and improved reproductive yields.

The general determination of the effectiveness of a PCV2 vaccine is well within the skills of the routine practitioner. This can for instance be done by monitoring the immunological response following vaccination or by testing the appearance of clinical symptoms or mortality after a challenge infection, e.g. by monitoring the targets' signs of disease, clinical scores, serological parameters, or by re-isolation of the challenge pathogen, and comparing these results to a vaccination-challenge response seen in mock vaccinated animals. Specifically, vaccine efficacy and protection can be measured by serologic determination of PCV2-specific antibody levels; by virus detection in serum or in animal secretions (oral, nasal, faecal, urinary); or by detecting other pathogens involved in PCVAD, via PCR, (immuno-)histology, hybridisation, or serologically.

For the PCV2 vaccines according to the invention, the efficacy is preferably determined by assessing the level of reduction of PCV2 infection in vaccinated versus unvaccinated groups, whereby such infection can be acquired naturally e.g. under field conditions, or can be deliberate, e.g. resulting from challenge under experimental conditions.

Depending on the type of adjuvant used, PCV2 vaccine efficacy can be based more on humoral- or on cellular immunity. Induced antibody titres can be measured e.g. using one of many available commercial PCV specific ELISA kits.

Various embodiments, preferences and examples of a vaccine according to the invention will be outlined below.

In an embodiment of the vaccine according to the invention comprising the mutant PCV2b ORF2 protein having a Proline at amino acid position number 131, the mutant PCV2b ORF2 protein is in the form of virus-like particles.

Typically a vaccine comprises a "pharmaceutically acceptable carrier" which comprises the antigen, and may assist in the manufacture, application, or conservation of a vaccine, without causing (severe) adverse effects. Such a carrier can be an aqueous solution, for example a buffer or a culture medium.

A preferred pharmaceutically acceptable carrier for the vaccine according to the invention is an insect cell culture medium, phosphate-buffered saline (PBS), or a combination thereof.

In addition the pharmaceutically acceptable carrier can comprise further additives and excipients, such as a filler, stabiliser, preservative, surfactant, or adjuvant. Details and examples are well-known, for instance as described in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

In addition, the vaccine according to the invention may comprise an adjuvant. Especially for such subunit vaccines this can significantly increase the target's immune response against the subunit antigen.

Therefore in an embodiment, the vaccine according to the invention comprises an adjuvant.

An "adjuvant" is a well-known vaccine ingredient that stimulates the immune response of a target in a non-specific manner. Many different adjuvants are known in the art. Examples of adjuvants are: Freund's Complete and -Incomplete adjuvant, vitamin E or alpha-tocopherol, non-ionic block polymers and polyamines such as dextran sulphate, Carbopol™, pyran, Saponin, such as: Quil A™, or Q-vacT™. Saponin and vaccine components may be combined in an ISCOM™.

Furthermore, peptides such as muramyldipeptides, dimethylglycine, tuftsin, are often used as adjuvant, and mineral oil e.g. Bayol™, Drakeol™, Klearol™, or Marcol™, Montanide™ or light mineral (paraffin) oil; non-mineral oil such as squalene, squalane; vegetable oils or derivatives thereof, e.g. ethyl-oleate. Also combination products such as ISA™ (Seppic), or DiluvacForte™ and Xsolve™ (both MSD Animal Health) can advantageously be used. A further option is the use of SVEA adjuvant (comprising squalane and vitamin E-acetate) as disclosed in EP 16206789.

A handbook on adjuvants and their uses and effects is: "Vaccine adjuvants" (Methods in molecular medicine, vol. 42, D. O'Hagan ed., 2000, Humana press, NJ, ISBN: 0896037355).

An adjuvant can be used in different formulations of a vaccine according to the invention, to enhance the immunoresponse to the mutant PCV2b ORF2 protein. For example, when the adjuvant is an oily substance, the oily phase can provide a depot effect in the vaccinated animal by slowly releasing the antigen, thereby providing a prolonged stimulation of the target's immune system.

The oily substance can be combined in different ways with the aqueous phase comprising the ORF2 protein. In an embodiment the vaccine according to the invention, can be formulated as an emulsion of a watery- and an oily phase; preferably the emulsion is of the type: water-in-oil (w/o), oil-in-water (o/w), water-in-oil-in-water (w/o/w), or is a double oil-emulsion.

More preferred is a vaccine according to the invention that is adjuvated with an oil, and is formulated as an oil-in-water emulsion. Such a vaccine advantageously displays properties both of direct immune stimulation from the watery phase, and of prolonged immune stimulation from the depot effect of the oily phase.

Therefore, in an embodiment of the vaccine according to the invention, the vaccine is formulated as an oil-in-water emulsion.

Methods and equipment for the preparation of an adjuvated vaccine emulsion at any desired scale is available commercially, for example for homogenisation using equipment such as from: Silverson, Ultra Turrax™, a Dispax reactor (IKA), or a Microfluidiser (Microfluidics).

The oil-in-water emulsion of the vaccine according to the invention preferably has a size of the particles of the dispersed phase that is quite small, preferably below 1 micrometre; such emulsions are commonly called "submicron emulsions".

In an embodiment of the oil-in-water emulsion of the vaccine according to the invention, the emulsion is a submicron emulsion.

In an embodiment of the vaccine according to the invention, the adjuvant is selected from the group consisting of: a light mineral oil, a Montanide, Emunade, and SVEA.

Such adjuvants are known to have favourable effects on the immunogenicity of porcine vaccines.

In an embodiment of a vaccine according to the invention, the vaccine is an oil-in-water emulsion and the adjuvant is a mineral oil.

In a preferred embodiment of the vaccine according to the invention, the mineral oil is a light- or white mineral oil or paraffin oil, commercially available under trade names such as: Marcol™ (ExxonMobil), Klearol™ (Sonneborn), or Drakeol™ (Penreco).

More preferred is the use of an additional adjuvant, specifically: a Vitamin E, e.g. alpha tocopherol or alpha tocopherol acetate.

In a preferred embodiment a vaccine formulation for the invention comprises an oil-in-water emulsion with surfactant, light paraffin oil and alpha tocopherol acetate. More preferred is a formulation wherein the surfactant is Polysorbate 80 (Tween™ 80), and/or the paraffin oil is Marcol™ 52, and/or the Vitamin E is alpha tocopherol acetate. Most preferred is a formulation with Microsol Diluvac Forte™, or with Xsolve™ (both: MSD Animal Health).

A further advantageous effect of the vaccine according to the invention, is the prevention or reduction of the spread of PCV2 in a porcine herd: vertically to offspring, and/or horizontally within the herd or population and within a geographical area. Consequently, the use of a vaccine according to the invention leads to a reduction of the prevalence of PCV2.

Therefore in a preferred embodiment of the vaccine according to the invention, the vaccine is for reducing the prevalence of PCV2 in a porcine population or in a geographical area.

In an embodiment the vaccine according to the invention may also comprise a stabiliser. This may serve to improve the characteristics of the vaccine emulsion, to protect degradation-prone components, and/or to enhance the shelf-life of the vaccine. Generally such stabilisers are large molecules of high molecular weight, such as lipids, carbohydrates, or proteins; for instance milk-powder, gelatine, serum albumin, sorbitol, sucrose, trehalose, spermidine, a protein-hydrolysate, Dextrane or polyvinyl pyrrolidone, and buffers, such as alkali metal phosphates.

Preferably the stabiliser is free of compounds of animal origin (animal compound free, ACF), or even: is chemically defined, for example as is disclosed in WO 2006/094974.

A vaccine according to the invention may comprise a preservative, such as thimerosal, merthiolate, phenolic compounds, and/or gentamicin. Preferably no preservative is employed.

It goes without saying that admixing other additives, that are required or beneficial to the pharmaceutical stability or to the effectiveness of the vaccine according to the invention, is well within the routine capabilities of the skilled person, and is therefore within the scope of the invention.

The animal targets for the vaccine according to the invention are porcines. The age, weight, sex, immunological status, and other parameters of the target to be vaccinated are not critical, although it is evidently favourable to vaccinate healthy, uninfected animals, and to vaccinate as early as possible to prevent any field infection with PCV2. Because such an infection can be established already at young age.

Therefore in an embodiment of the vaccine according to the invention, the vaccine is applied to young porcine animals shortly after birth, preferably within 28 days after birth, more preferably within 21, 14, 12, 10, 8, 7, 6, 5, 4, 3, 2 or even within 1 day after birth, in this order of preference.

Alternatively the vaccine according to the invention can be administered to a pregnant sow, to provide piglets with maternally derived PCV2 specific antibodies, either by transplacental passage, and/or by transfer via colostrum.

Advantageously, the efficacy of the vaccine according to the invention is not influenced to any large extent by the level of maternally derived antibodies against PCV2 that the young porcine animals may have acquired from their mother; 'young' referring to an age of 4 weeks or less.

Therefore in an embodiment of the vaccine according to the invention, the vaccine is applied to young porcine animals carrying maternally derived antibodies against PCV2.

The vaccine according to the invention can also serve as an effective priming vaccination, which can later be followed and amplified by a booster vaccination. For example, the vaccine according to the invention can be administered to a piglet at about 2-10 days of age, and again about 3 weeks later, with each vaccination at a volume of about 1 ml.

However, as the vaccine according to the invention is effective already after a single administration, a preferred embodiment is the administration of a single dose, e.g. of about 2 ml, from about 3 weeks of age. This vaccination protects pigs during the whole of the fattening period, till about 5-6 months of age.

When the porcine target of the vaccine according to the invention is intended to be kept for more than 6 months, such as sows for breeding, or boars for producing sperm, these can be administered a regular booster vaccination, 1, 2, or 3 times per year, e.g. for sows: one booster vaccination before each farrowing, which is on average about 2.2 times/year.

For the invention "about" indicates that a number can vary between ±25% around its indicated value. Preferably "about" means±20% around its value, more preferably "about" means±15, 12, 10, 8, 6, 5, 4, 3, 2% around its value, or even "about" means±1% around its value, in that order of preference.

A vaccine according to the invention can be used either as a prophylactic- or as a therapeutic treatment, or both, as it interferes both with the establishment and with the progression of an infection by PCV2 or associated diseases.

Preferably a vaccine according to the invention is formulated into a form that is suitable for parenteral injection, i.e. as an injectable liquid such as: a suspension, solution, dispersion, or emulsion.

The regime for the administration of a vaccine according to the invention preferably is integrated into existing vaccination schedules of other vaccines that the target porcine may require, in order to reduce stress to the animals and to reduce labour costs. These other vaccines can be administered in a simultaneous, concurrent or sequential fashion, in a manner compatible with their registered use.

The vaccine according to the invention comprises between about 0.1 and about 1000 micrograms of PCV2b ORF2b-131P protein per animal dose. Preferably the vaccine comprises between 0.5 and 500 µg, between 1 and 250, or even between 2 and 200 µg of PCV ORF2b-131P protein per animal dose, in this order of preference. The selection of the amount of protein per dose can be made by the skilled person, based on characteristics of the vaccine and of the target animal.

The amount of ORF2b-131P protein per animal dose can be determined in the ready vaccine emulsion, using standard biochemical laboratory procedures, for example by breaking the emulsion, and testing the water-phase using SDS-PAGE.

Determining amounts is then done by comparing to known amounts of a reference protein, e.g. bovine serum albumin. See e.g.: The Protein Protocols Handbook, 2nd edition, September 2002, ed. J. M. Walker, Humana Press Inc., Totowa, N.J.; Chapter 29, p. 237-242.

Alternatively ORF2 protein quantification can be done using mass-spectrometry.

Preferably the amount of PCV ORF2b-131P protein per animal dose is determined in a watery bulk of the antigen phase, before mixing and/or emulsification with an oily phase.

A vaccine according to the invention, can be administered in a volume that is acceptable for the target animal, and can for instance be between about 0.1 and about 10 ml in volume. Preferably one dose is in a volume between about 0.1 and about 5 ml, more preferably one animal dose is between 0.2 and 3 ml.

When administered by intramuscular route, the volume of one dose is preferably between about 1 and about 3 ml, more preferably about 2 ml; When administered by intradermal route, the volume of one dose is preferably between about 0.1 and about 0.5 ml, more preferably about 0.2 ml.

The vaccine according to the invention can be administered to a target porcine according to methods known in the art. Preferred application is by parenteral route, i.e. through the skin, e.g.: intramuscular, intraperitoneal, intradermal, submucosal, or subcutaneous. More preferred route of administration of the vaccine according to the invention is by intramuscular or by subcutaneous injection. Even more preferred is administration intramuscularly in the hind-leg, or in the neck.

It goes without saying that the optimal route of application will depend on the specifics of the vaccine that is used, and on the particular characteristics of the target.

In an embodiment the vaccine according to the invention is administered intramuscularly to a porcine from about 3 weeks of age, as a single dose of about 2 ml.

Preferred site for intramuscular administration is the neck.

In an embodiment the dose volume of the administration of the vaccine according to the invention by intramuscular route is flexible, i.e. the vaccine is administered either as a single dose of 2 ml/animal, or as two consecutive doses of 1 ml/animal. When administered as two doses, both are preferably separated in time by at least 1 week, preferably by 2-5 weeks, more preferably by about 3 weeks.

In an embodiment the vaccine according to the invention is administered intradermally to a porcine from about 3 weeks of age, as a single dose of about 0.2 ml.

Preferred site for intradermal administration is selected from: the neck, the back, and the hind leg.

It is well within reach of the skilled person to further optimise a vaccine according to the invention. Generally this involves the fine-tuning of the efficacy of the vaccine to further improve its provided immune-protection. This can be done by adapting the dose, volume, or antigen content of the vaccine; by using the vaccine in another form or formulation; by adapting the other constituents of the vaccine (e.g. the stabiliser or the adjuvant); or by application via a different route, method, or regime. All these are within the scope of the invention.

A vaccine according to the invention may additionally comprise other compounds, such as an additional antigen, a cytokine, or an immunostimulatory nucleic acid comprising an unmethylated CpG, etc. Alternatively, a vaccine according to the invention can advantageously be combined with a pharmaceutical component for example an antibiotic, a hormone, an anti-inflammatory- or an anti-parasitic drug. Or, the vaccine according to the invention, may itself be added to a vaccine.

The vaccine according to the invention can advantageously be combined with one or more further antigen, e.g. derived from another porcine pathogen. The advantage of such a combination vaccine is that it not only induces an immune response against PCV2, but also against other pathogens while only a single handling of the target animal for the vaccination is required, thereby reducing vaccination-stress to the animal, as well as reducing time- and labour costs.

Therefore, in a preferred embodiment the vaccine according to the invention comprises a further antigen of a micro-organism pathogenic to porcine animals.

The "further antigen" may itself be an infectious micro-organism, or be inactivated, or a subunit, and may be with or without an adjuvant. The further antigen may consist of a biologic or synthetic molecule such as a protein, a carbohydrate, a lipopolysacharide, a lipid, or a nucleic acid molecule. Alternatively it may be an expression product from a nucleic acid from that other micro-organism, or a vector comprising such a nucleic acid; the vector can be itself a micro-organism or a eukaryotic host cell.

The further antigen can be "derived from" the other micro-organism pathogenic to porcine in any way, e.g. as an extract, fraction, lysate, homogenate or sonicate.

A "micro-organism pathogenic to porcine animals" for the invention, is well known in the art. The further antigen may therefore be derived in principle from any virus, bacterium, parasite, fungus, rickettsia, protozoa and/or parasite that is pathogenic to porcines.

Examples of such micro-organism pathogenic to porcine animals are: porcine reproductive and respiratory syndrome virus (PRRSV), pseudorabies virus, porcine parvo virus, classical swine fever virus, swine influenza virus, foot-and-mouth disease virus, porcine epidemic diarrhoea virus, transmissible gastro-enteritis virus, vesicular stomatitis virus, *Mycoplasma hyopneumoniae, Lawsonia intracellularis, Actinobacillus pleuropneumoniae, Haemophilus parasuis, Escherichia coli, Streptococcus suis*, or a *Salmonella, Brachyspira, Clostridia, Pasteurella, Erysipelothrix, Bordetella, Toxoplasma, Isospora*, or *Trichinella*.

In a preferred embodiment of the vaccine according to the invention, the vaccine comprises—next to antigen from PCV2—one or more antigen from a micro-organism pathogenic to porcine animals selected from the group consisting of *M. hyopneumoniae, L. intracellularis*, and PRRSV.

As these are currently the most prominent porcine pathogens, therefore their combination into a single shot, ready-to-use vaccine is very favourable, both from economic as well as from veterinary viewpoint.

In a preferred embodiment the one or more further antigen is added to a vaccine according to the invention as a lyophilised preparation, whereby the combination vaccine is prepared by reconstitution with the vaccine emulsion of the invention. This is described for example in WO 2010/106095.

In a preferred embodiment the vaccine according to the invention is a combination vaccine comprising the mutant PCV2b ORF2 protein and an antigen from *M. hyopneumoniae*, and said combination vaccine is used to reconstitute a lyophilised preparation of an antigen from *L. intracellularis* and/or from PRRSV.

In a preferred embodiment the vaccine according to the invention is a combination vaccine comprising the mutant PCV2b ORF2 protein, an antigen from *M. hyopneumoniae*, and an antigen from L. intracellularis, and said combination vaccine is used to reconstitute a lyophilised preparation of an antigen from PRRSV.

In a further aspect, the invention relates to a method for reduction of infection by PCV2 or of associated signs of disease in a porcine animal, the method comprising the administration to said porcine of the vaccine according to the invention.

A vaccine according to the invention can be prepared by means well-known to the skilled person. As described the use of a mutant PCV2b ORF2 protein as described for the invention, or of the insect cells as described for the invention, allows the manufacture of a vaccine for porcines, as described for the invention. In this regard, the mutant PCV2b ORF2 protein is also obtainable by a method according to the invention.

Therefore in a further aspect the invention relates to the use of mutant PCV2b ORF2 protein having a Proline at amino acid position number 131, for the manufacture of a vaccine for porcine animals for reduction of infection by PCV2 or of associated signs of disease.

In a further aspect the invention relates to mutant PCV2b ORF2 protein having a Proline at amino acid position number 131, for use in a vaccine for porcine animals for reduction of infection by PCV2 or of associated signs of disease.

In a further aspect the invention relates to a process for preparing a vaccine according to the invention, the process comprising one or more steps selected from:
admixing mutant PCV2b ORF2 protein having a Proline at amino acid position number 131, with a pharmaceutically acceptable carrier; and
formulating said admixture of mutant PCV2b ORF2 protein and pharmaceutically acceptable carrier with an adjuvant.

For use in the process for preparing a vaccine according to the invention, the mutant PCV2b ORF2 protein is obtainable by a method for the expression of mutant PCV2b ORF2 protein in the insect cells according to the invention, and/or is obtainable by a method for the production of mutant PCV2b ORF2 protein according to the invention.

In an embodiment of the process for preparing a vaccine according to the invention, the mutant ORF2 protein is in the form of VLPs.

A vaccine according to the invention can be prepared by a skilled person, in a form that is suitable for administration to a porcine target, and that matches with the desired route of application, and with the desired effect. Commonly such vaccines are prepared sterile, and at physiological pH.

Details and examples of a method, a use, or a process for preparing a vaccine according to the invention, are described herein, and such procedures are readily applicable by a person skilled in the art using routine materials and methods. For example, the mutant PCV2b ORF2 protein as described for the invention can be produced in insect cells at industrial scale, and is then combined with pharmaceutically acceptable excipients, is formulated into a vaccine, e.g. by emulsification with an oily adjuvant, and filled-out into appropriately sized containers. The various stages of the manufacturing process will be monitored by adequate tests, for instance by immunological tests for the quality and quantity of the antigens; by microbiological tests for inactivation, sterility, and absence of extraneous agents; and ultimately by vaccination-studies in animals for confirming efficacy and safety. After completion of the testing for quality, quantity and sterility the vaccine product can be released for sale.

All these are well known to a skilled person, and general techniques and considerations that apply to the preparation of vaccines are described for instance in governmental directives and regulations (Pharmacopoeia, 9CFR) and in well-known handbooks (Pastoret, Lippincot, supra).

The invention will now be further described by the following, non-limiting, examples.

EXAMPLES

Example 1: Assembly of Different PCV2 ORF2 Expressing Recombinant Constructs

For the expression of PCV2 ORF2 proteins in insect cells, recombinant baculoviruses were generated, using standard procedures. In short:

The wildtype PCV2 ORF2 genes used in these experiments were obtained from different sources: the PCV2a parental virus was from a vaccine strain from USA; PCV2b was from French isolate Imp1011, GenBank acc. nr. AF055394; PCV2d was from China, strain BDH, GenBank acc.nr: HM038017.

The ORF2 gene was subcloned by amplification using PCR, and insertion into a cloning plasmid. Next, some of the ORF2 genes were mutated, either to encode a Proline at amino acid position 131, by using PCR-directed mutation. Alternatively, or additionally, ORF2 genes were codon-optimised to resemble the codon usage table of the AcMNPV polyhedrin gene. The mutated sequences used herein for PCV2b are presented in the attached sequence listing, as described.

Synthetic constructs of mutated ORF2 gene inserts were ordered from a commercial supplier (BaseClear, Netherlands; or Genscript, Piscataway, N.J., USA).

For use with the Bac-to-Bac system these were subcloned into cloning vector pFastBac1, and for use with the ProEasy system in transfervector pVL1393. In both instances the insert was behind the polyhedrin promoter. Generation and selection of recombinant baculovirus was performed according to the manufacturer's instructions. Some of the PCV2a recombinant baculovirus constructs had been constructed using the classical selection technique of transfection and isolation of recombinants by plating of infected insect cells under soft agar, and plaque picking.

All recombinant baculoviruses were amplified on Sf9 cells, harvested, stored refrigerated or frozen, and were titrated. Virus stocks used for further experiments were typically between 7.5 and 8.5 Log 10 TCID50/ml.

A selection of the recombinant baculoviruses used for the expression of PCV2 ORF2 protein in insect cells is listed in the below schedule:

NB: All inserts were inserted behind the polyhedrin promoter. Codon optimisation (when applied) was towards the codon use of the AcMNPV polyhedrin gene.

| Virus number | PCV2 genotype | Baculovirus construct | Codon optimisation | Amino acid at 131 |
|---|---|---|---|---|
| 1 | 2a | plaque picked | None | Proline |
| 2 | 2a | plaque picked | Yes | Proline |
| 3 | 2a | Bac-to-Bac | None | Proline |
| 4 | 2a | Bac-to-Bac | Yes | Proline |
| 5 | 2a | ProEasy | Yes | Proline |
| 6 | 2b | Bac-to-Bac | None | Threonine |
| 7 | 2b | Bac-to-Bac | Yes | Threonine |
| 8 | 2b | Bac-to-Bac | None | Proline |

-continued

| Virus number | PCV2 genotype | Baculovirus construct | Codon optimalisation | Amino acid at 131 |
| --- | --- | --- | --- | --- |
| 9 | 2b | ProEasy | Yes | Proline |
| 10 | 2d | ProEasy | Yes | Proline |

Example 2: Expression in Insect Cells

The different recombinant baculovirus constructs, as described above, were used to infect insect cells, and express several variants of the PCV2 ORF2 protein. The protein produced was visualised and analysed to assess the effect of the various mutations made, by comparing to unmodified protein, or to protein of another genotype of PCV2. Some recombinant baculoviruses were scaled-up, to produce protein for the formulation of PCV2 subunit vaccine for testing in pigs.

2.1 Insect Cell Cultures

Standard infection and expression experiments were done at small scale, using Sf9 insect cells, which were taken from a spinner culture of clean cells that were regularly split to maintain exponential growth. Typical infection rates were between 0.01 and 0.1 moi, and culture durations were between 3 and 5 days. Cultures were monitored regularly by light microscopy to check the health of uninfected cells, or to monitor the progress of viral replication in infected cultures.

Culture vessels used were either T25 or T75 flasks (Falcon) with monolayer cultures of 5 or 15 ml respectively. Alternatively 100 ml suspension cultures were run in spinner flasks (Corning). Flasks were incubated at 27° C., and the culture medium used was Sf-900™ II (Thermo Fisher scientific). No serum was added, but a mixture of antibiotics: 50 µg/ml gentamycin and 0.25‰ natamycin.

When most of the cells showed cytopathogenic effect (cpe), the cultures were harvested: T-flask cultures required tapping firmly to loosen the cells. Culture-harvests were then centrifuged, and culture supernatant was discarded as the ORF2 protein produced was mostly contained within the insect cells. Depending on the intended further use the cell-pellet could then be resuspended in a required liquid at a desired concentration.

The small scale cultures were not routinely inactivated; samples were either used in containment facilities, or were treated with denaturing electrophoresis sample buffer, and then considered inactivated.

Large scale cultures followed essentially the same outline, with adaptations for volume and equipment. In experimental setting, intermediate large scale insect cell suspension cultures were run at 2 to 10 litre volume, in industrial fermenters with automated process controls. Clean Sf9 insect cells were obtained from a pre-culture. Moi was between 0.01 and 0.1, and culturing was for 5-7 days. When the infection had progressed sufficiently, the cells were left to settle by gravity. Then the top 90% of the culture volume was removed, the cells were harvested in 1/10th of the original culture volume, and were lysed by sonification. At medium scale sonification was performed batch-wise, on ice, using a tip sonifier (Vibra Cell™, Sonics, CT, USA). At larger scales (100 l volumes or more), sonication was done by passage through a flow-through sonication cell (Sonobloc™, Bandelin)

Next the sonicate was inactivated using BEI. This was then neutralised using Na-thiosulphate. Then the inactivated harvest was clarified by centrifugation and the supernatant containing the ORF2 protein, was kept as the watery phase of the bulk antigen. This was stored at 2-8° C. for quality control and further processing. In these products the pharmaceutically acceptable carrier for the antigen is thus spent medium from the insect cell culture. When needed the bulk antigen could be concentrated, of could be dialysed against PBS. Alternatively the antigen could be diluted with fresh insect cell culture medium, or with PBS.

2.2 ELISA 2.2.1 Outline of ELISA Insect cell cultures were infected with recombinant baculoviruses number 6 (Threonine at 131), or virus number 8 (T131P substitution), to test the effect of the T131P substitution in PCV2b ORF2 protein. Both are constructs in Bac-2-Bac format, and did not have codon-optimisation. Of virus 6, two isolates were tested.

T175 flask cultures of Sf9 cells were infected, incubated, and harvested by centrifugation of the whole culture. The cell pellets were taken up into 10 ml water-for-injection, which effectively lysed all the cells. The cell-lysates were then tested for their antigenic mass in a sandwich ELISA, briefly as follows:

The wells of a polystyrene micro-titration plate were coated with a monoclonal antibody directed against PCV2 ORF2a. Serial dilutions of lysate samples were incubated alongside a series of dilutions of a known reference standard of PCV2a ORF2. Next the plates were incubated with a fixed amount of a secondary antibody also directed against PCV2 ORF2a, which was conjugated with biotin. Finally the amount of bound conjugate was then quantified by incubation with peroxidase-conjugated streptavidin, followed by chromophoric detection by automatic plate reader.

The amount of antigen in the lysates was calculated against the reference standard, of which the amount of antigen was arbitrarily set at 100 antigenic units (AU)/ml.

2.2.2 Results and Conclusions of ELISA

The amount of ORF2 protein detected in the lysates was as follows:

virus 6 infected cells (two variants): 5.5 and 7.4 AU/ml,
virus 8 infected cells: 68 AU/ml.

A lysate prepared in pure water from the cells infected with the recombinant virus expressing PCV2b ORF2 protein without mutation at 131, contained only very little ORF2 protein as detected by ELISA. However such a lysate from cells infected with recombinant baculovirus expressing ORF2 with the T131P substitution, contained about 10 times more protein.

These ELISA results illustrated the big difference in the amount of ORF2 protein that could be readily isolated from infected insect cells, with or without the substitution of ORF2 amino acid number 131. On the one hand this related to the ease with which the protein was released in a non-denaturing lysate. On the other this also reflected the difference in overall production of PCV2b ORF2 protein in insect cells, without or without mutation of the amino acid at position 131.

2.3 Immunofluorescence Assays 2.3.1 Outline of IFT Assays

For Immunofluorescence tests (IFTs) clean insect cells were seeded in the wells of a 96-well microtitration plate, typically at $2.5 \times 10^{4}$ cells per well, in 100 µl of medium. After attachment the cells were infected with the particular recombinant baculovirus to be investigated. Typically dilution ranges of the virus were inoculated to allow observation at different moi's. The plates were analysed after 4-5 days of incubation, when the insect cells had become properly infected but were not yet lysed. The medium was removed, the cells were fixed with cold ethanol, and stained with appropriate antibodies according to standard procedures. A FITC-conjugated second antibody was used for the visualisation. The insect cells were counter-stained with Evans blue to enhance the contrast with the background.

For these IFT studies the primary antibody used was a swine polyclonal anti-PCV2a antiserum, this was sufficiently potent to also stain ORF2 protein of PCV2b and PCV2d genotype.

2.3.2 Results of IFT Assays

When comparing the IFT results observed for the different ORF2 protein expression products, several observations were made:

- The recombinant viruses 1-5 as described above, all expressing PCV2a ORF2 protein, invariably all caused a cytoplasmic staining pattern whereby essentially the whole of the insect cell was showed a bright colouration.
- However insect cells infected with recombinant baculovirus number 6, expressing wildtype PCV2b ORF2 protein, displayed an essentially different pattern, where the staining was located exclusively around the nucleus of the insect cells. No cytoplasmic staining was observed.
- This IFT pattern was largely the same for insect cells infected with virus number 7, which is also expressing PCV2b ORF2 protein but from a codon-optimised gene. Only difference was that a small amount (approximately 10% of the insect cells) showed cytoplasmic staining, while the majority of the cells still displayed nuclear staining.
- Surprisingly, insect cells infected with virus number 8 gave an IFT pattern where the fluorescence pattern was the reverse of that for recombinant virus number 7: most of the insect cells displayed cytoplasmic staining, with some cells still showing nuclear staining. Virus number 8 carried a PCV2b ORF2 gene wherein the codon encoding amino acid number 131 had been mutated from a Threonine to a Proline (T131P).
- Finally, insect cells infected with virus number 9 (PCV2b ORF2 gene with codon optimisation and carrying the T131P substitution, in a clean construct) all exclusively showed cytoplasmic staining.
- Remarkably, insect cells infected with recombinant baculovirus number 10 (encoding PCV2d ORF2 protein with the T131P substitution, codon-optimisation, and in a clean construct) all still displayed a nuclear staining pattern.

2.3.3 Conclusions from IFT Assays

It was concluded that the effective expression of ORF2 protein from PCV2b in insect cells, required the substitution of the amino acid at position number 131 by Proline, displaying a cytoplasmic staining pattern, in an IFT with an anti-PCV2a antibody. Without such mutation, the PCV2b ORF2 protein displayed a staining exclusively at or around the nucleus of the insect cell expressing that protein.

The mutation of the ORF2 gene by codon optimisation only, gave a slight shifting of the IFT staining pattern, probably as a result of the increased efficiency of the expression.

The nuclear staining pattern could be further reversed when the recombinant baculovirus was not based on a construct containing residual elements from the cloning vector (such as in a recombinant produced using the Bac-to-Bac system), but was a 'clean' baculovirus construct, i.e. not contain further genetic elements from the recombination process in its genome. Such clean recombinant baculoviruses can be obtained by using classical homologous recombination and plaque purification, or more conveniently by using a commercial kit such as the ProEasy system.

Thus: a reversion of the IFT nuclear staining pattern observed in insect cells expressing PCV2b ORF2 protein, can be obtained by mutation of the triplet encoding the ORF2 amino acid number 131 to encode Proline. Further optimisation of cytoplasmic ORF2 protein expression can be reached by codon-optimising the encoding gene, and by using a clean recombinant baculovirus construct.

2.4 Quantification by Gel-Electrophoresis 2.4.1 Outline of Gel-Electrophoresis Assays To allow a quantification of the expression level of the different ORF2 proteins, samples from infected insect cell cultures were run on SDS-PAGE, alongside lanes with known quantities of bovine serum albumin (BSA) as marker protein. After staining, the gels were scanned and analysed. By using a strongly denaturing sample buffer this experiment revealed the total expression capacity of insect cells infected with the various recombinant baculovirus constructs The different recombinant baculoviruses to be tested were cultured in T75 flasks as described, harvested, centrifuged, and the cell pellets were taken up in 7.5 ml PBS. Samples of the supernatant and of the resuspended cells were then taken up into standard denaturing Laemmli SDS-PAGE sample buffer (containing bromophenol blue indicator and beta-mercaptoethanol).

Samples were run on standard poly-acrylamide gels (pre-cast Criterion TGX™, Any kD (15%), Bio-Rad), in standard Tris-Glycine-SDS running buffer. After the electrophoresis, the gels were stained with Instant Blue™ (Expedeon). Finally the gels were digitised and analysed with a Bio-Rad GS-900 calibrated densitometer using Image Lab™ Software, version 5.2.1, to assign an amount of protein to individual bands on the gel.

2.4.2 Results of Gel-Electrophoresis Assays

In FIGS. 1 and 2 some representative images are presented of gel such as used in these experiments: FIG. 1: samples from cultures of insect cells infected with viruses no. 3, 6, or 7; and FIG. 2: samples from cultures with viruses no. 8 or 9. Per type of virus, the first lane contains a sample of culture supernatant, the next three lanes contain samples of the 2× concentrated cells, with 30, 20, and 10 µml from left to right. Left- and right-most lanes: molecular weight markers 10-250 kDa (Precision Plus Protein™ Standards, Bio-Rad), the band sizes are indicated in the Figures.

Each gel also contained a dilution range of BSA (Albumin Standard high-quality, Thermo Fisher Scientific), that was used as a 100 ng/µl solution. The amounts used were: FIG. 1: in lanes 14-17: 0.25, 0.5, 1, and 2 µg BSA; FIG. 2: in lanes 11-15: 0.25, 0.5, 1, 2, and 3 µg BSA.

The analyses by densitometer focussed on the bands of PCV2 ORF2 protein, at 26 kDa. All samples were analysed on gels two times, the calculated yield results are averages of the Duplo's.

The yields of PCV2 ORF2 protein are expressed in micrograms of protein per ml of the original T75 culture (15 ml volume). The yields were found to be as follows:

| Virus no. | PCV2 genotype | Baculovirus construct | Codon optimisation | Amino acid at 131 | ORF2 yield (µg/ml) |
|---|---|---|---|---|---|
| 3 | 2a | Bac-to-Bac | None | Proline | 32 |
| 6 | 2b | Bac-to-Bac | None | Threonine | 26 |
| 7 | 2b | Bac-to-Bac | Yes | Threonine | 36 |

-continued

| Virus no. | PCV2 genotype | Baculovirus construct | Codon optimisation | Amino acid at 131 | ORF2 yield (μg/ml) |
|---|---|---|---|---|---|
| 8 | 2b | Bac-to-Bac | None | Proline | 58 |
| 9 | 2b | ProEasy | Yes | Proline | 76 |

Several observations could be made:

- For virus infections with viruses numbers 8 and 9, the two constructs of PCV2b ORF2 with T131P substitution, the gel lanes (see FIG. 2) looked slightly darker than for the other viruses tested, even though for all cultures compared by SDS-PAGE the moi (0.1), culture time (4 days), and other conditions were all the same. This could indicate that the infection may not have progressed as far as for the other viruses, resulting in more cell-material in the sample. Perhaps the Proline substitution caused a slight attenuation of the recombinant baculovirus. However protein-expression levels appeared unaffected and were better than for PCV2b ORF2 without this mutation.
- None of the samples of supernatant showed an amount of ORF2 protein that could be visualised by the CBB staining that was used. Consequently, under the conditions as applied in these experiments, effectively all of the expressed ORF2 protein was contained in the insect cells.
- The expression level of unmutated PCV2b ORF2 protein (virus 6) was lower than that of PCV2a ORF2 (virus 3), with 26 versus 32 μg/ml. It is reminded that these samples display the total of all protein produced, because of the aggressive denaturation employed (boiling in SDS and beta-mercaptoethanol). This indicates that the total protein expression from the unmutated PCV2b ORF2 gene is actually lower over-all in insect cells.
- NB: This difference in yield is much worse in practice, when harvesting is without (strong) denaturation. In that case lysates from insect cells expressing unmutated PCV2b ORF2 hardly showed any detectable ORF2 protein at all.
- The yield of unmutated PCV2b ORF2 protein could be slightly increased by the use of a codon optimised ORF2 gene: compare the yields of virus-cultures 6 and 7, with total yields of 26 and 36 μg/ml respectively.
- However the most significant increase was achieved by the introduction of the T131P substitution in the PCV2b ORF protein, see the yields of virus-cultures 6 and 8, with 26 versus 56 μg/ml. The T131P substitution was thus able to cause more than a doubling in total yield of ORF2 protein, even in these small scale cultures without any optimisation.
- Even better yields of PCV2b ORF2 protein could be reached when all mutations were combined: T131P substitution, codon optimisation and using a clean baculovirus construct: comparing the yields of virus-cultures 6 and 9, shows a tripling of protein yield, from 26 to 76 μg/ml.

A similar analysis of protein yield was also performed on samples that had been produced in intermediate large scale cultures of 2 litres. Harvests were obtained in 7.7× concentration compared to the total culture volume. The ORF2 protein from these cultures was also used to produce the experimental PCV2 vaccines described hereafter.

ORF2 protein yields obtained were as follows, indicated in μg/ml of the original 2 litre culture volume:

| Virus no. | PCV2 genotype | Baculovirus construct | Codon optimisation | Amino acid at 131 | ORF2 yield (μg/ml) |
|---|---|---|---|---|---|
| 5 | 2a | ProEasy | Yes | Proline | 44.2 |
| 9 | 2b | ProEasy | Yes | Proline | 103.9 |

The culture conditions in the fermenters were clearly more optimal then in the small scale culture sin T-flasks. Not only because of the automated control of temperature, pH, and dissolved oxygen, but also because these were suspension cultures, which allow higher cell-densities per ml of culture.

The recombinant baculoviruses used were also constructed in the optimal way in the sense that they had a codon-optimised ORF2 gene, in a clean baculovirus construct (produced using the ProEasy system).

This resulted in a protein yield for insect cells infected with virus no. 9 of over 100 μg/ml of culture, while in T-flasks this was 76 μg/ml.

Remarkably the yield of protein from insect cells expressing mutant PCV2b ORF2 protein with the substitution of amino acid number 131 by Proline, was substantially higher than that of unmodified PCV2a ORF2 protein, even though the same constructs and culturing conditions were used. In particular because the ORF2 gene of the PCV2a used here also had a Proline at amino acid position 131 from its native sequence. It is not immediately apparent what might cause this difference, though it is evidently highly favourable for the production of PCV2b ORF2 protein for the manufacture of subunit vaccines against PCV2.

2.4.3 Conclusions from Gel-Electrophoresis Assays

Although not all effects observed could be explained at this time, the analysis by gel-electrophoresis made it explicitly clear that expression in insect cells of PCV2b ORF2 protein without any adaptation, at best yielded protein amounts lower than for the expression of PCV2a ORF2. This difference is even worse when the cells are harvested using non-denaturing conditions.

The lack in yield can however be more than made up by substituting the amino acid at position 131 in PCV2b ORF2 by Proline, which at least doubles the yield as compared to that of unmutated PCV2b ORF2 protein.

Even further increases in yield can be reached by expressing the 131P mutation from a codon-optimised ORF2 gene, and using a clean baculovirus construct. Still further improvements in the yields can be reached in large scale suspension cultures.

Together these findings enable for the first time the commercial and large-scale production of ORF2 protein from PCV2b genotype, by a recombinant expression system.

Example 3: Vaccination-Challenge Experiments in Pigs 3.1 Introduction 3.1.1 Objective This study was performed to compare and evaluate the efficacy of porcine vaccines based on insect-cell expressed mutant PCV2 ORF2 proteins according to the invention. To provide a thorough test of their protective capacity, the ORF2 proteins of different genotypes were used not only against a homologous, but also against a heterologous PCV2 challenge-infection. Also the vaccine doses used contained relatively low amounts of ORF2 protein.

3.1.2 Study Outline

For this study 140 piglets were used, allotted to 2 sets of 7 treatment groups with 10 animals each, one set for each of the two challenges. The 140 animals were derived from 14 sows. The piglets had detectable levels of anti-PCV2 ORF2 antibodies ranging from low to very high titres; the average MDA titre for all animals was 5.8 Log 2 by antibody-ELISA The piglets were vaccinated intramuscularly in the neck with 2 ml each, when they were approximately three weeks old. The vaccines used comprised different amounts of PCV2 ORF2 protein produced via the baculovirus-insect cell expression system, from one of three genotypes: PCV2a, 2b or 2d. The recombinant baculoviruses used were numbers 5, 9, and 10, as described above, having a Proline at amino acid position 131, expressed from an encoding ORF2 gene that was codon optimised towards the AcMNPV polyhedrin gene, and using a clean baculovirus construct. The vaccines were formulated as oil-in-water emulsions with Emunade™ adjuvant. The vaccine additionally contained antigen from *Mycoplasma hyopneumoniae* (J strain), to resemble the commercial vaccine: Porcilis™ PCV M Hyo. With regard to the PCV2 ORF2 antigen, the vaccine tested comprised either a quarter or a sixteenth of a standard full dose per animal.

For both sets, the division of the vaccine treatments over the groups was as indicated in the schedule below.

NB: Animals in group 7 of both sets were not vaccinated, to serve as challenge controls.

| Group | 1 | 2 | 3 | 4 | 5 | 6 | 7 |
|---|---|---|---|---|---|---|---|
| Vaccine dose (µg ORF2 prot./animal) | 20 | 5 | 20 | 5 | 20 | 5 | No vaccine |
| ORF2 protein genotype | 2a | | 2b | | 2d | | |

Two weeks post vaccination all animals were transported to the challenge facilities. At 3 weeks post vaccination (at 6 weeks of age), all animals received a challenge infection with virulent PCV2, either from 2b or from 2d genotype. Challenge was by way of intranasal administration of 6 ml (3 ml per nostril) of PCV2 in PBS, at 5 Log 10 TCID50/ml; using for set 1: a PCV2b challenge virus (Dutch isolate, 2003), and for set 2: a PCV2d challenge virus (German isolate, 2015). The challenge viruses had been produced on PCV-free PK15 cells, and had been checked for bacterial and fungal sterility.

Three weeks post challenge (at 9 weeks of age), all animals were euthanized and examined: the viscera were inspected in-situ, paying particular attention to: lungs, inguinal and mesenteric lymph nodes, tonsils, thymus, spleen, liver and kidneys. Next, samples from tonsil, lung, mesenteric lymph node and inguinal lymph node were removed and fixed for detection of PCV2 challenge virus, by immunohistochemistry (INC).

Other analyses were also performed, such as serology on blood samples, and qPCR on tissue and swab samples. However the IHC data gave the most explicit results.

3.2 Materials and Methods

3.2.1 Pcv2 Orf2 Proteins:

The PCV2 ORF2 gene sequences of PCV2a, 2b and 2d were produced in intermediate large scale cultures as described in section 2.1 above. Their quantification by gel-electrophoresis is described in section 2.3.2 above.

3.2.2 Test Animals

Test animals were negative for PCV2 viral load, and had moderate levels of anti-PCV2 antibodies. The test would have been rejected if any of the animals had developed clinical signs of PCV2 infection prior to challenge.

Only healthy animals were included in the trial. All piglets were observed daily for general health, and for clinical or systemic signs of disease, such as loss of appetite, reluctance to move, tendency to lie down, listlessness or drowsiness, shivering, bristling, oedema (especially around the eyes), vomiting and diarrhoea and dyspnoea.

Piglets were marked individually by ear-tags, with piglets of the 14 litters being equally divided over the test groups. After weaning tap water was available ad libitum and feeding was done according to standard procedures.

The vaccination was given at the farrowing farm. After transport to the challenging facilities one week acclimatisation was included.

3.2.3 Laboratory Experimental Procedures

3.2.3.1 Immunohistochemistry

Tissue samples were prepared for histological examination by fixing in 10% formalin and embedding in paraffin. Microscopy slides were prepared. These were incubated with a rabbit polyclonal anti-PCV2 serum as primary antibody, and visualised with peroxidase staining (Envision+™, DAKO). The slides were counterstained with hematoxylin. In the microscopic examination of tonsils and lymph nodes, characteristic brown staining was given a score depending on extent of colouring:

score 0: lymphoid follicles showed no specific positive staining;
score 1: less than 10% of the lymphoid follicles contained up to 15 cells with specific positive staining;
score 2: 10-50% of the lymphoid follicles contained up to 15 cells with specific positive staining, or less than 10% of the lymphoid follicles contained more than 15 cells with specific positive staining;
score 3: >50% of the lymphoid follicles contained cells with specific positive staining.

The sum of the scores of the individual tissues were recorded as the total IHC score per animal, and these were combined for all animals of a group.

3.2.3.2 Vaccine Formulations

The test vaccines were formulated as oil-in-water emulsions with Emunade™, this is a dual adjuvant with mineral oil dispersed in an aqueous phase containing the vaccine antigens as well as Aluminium-hydroxide. The preparation, with 9% Mhyo antigen, was according to the procedure as disclosed in WO 2016/091998.

Also the vaccine was prepared in line with EP 1.926.496, so that 25% of a full dose (2 ml/animal) comprised approximately 20 µg of ORF2 protein, and a 6.25% dose comprised 5 µg ORF2 protein/animal dose.

3.3 Results & Conclusions

By way of immunohistochemistry, the tissue samples of tonsil, mesenteric- and inguinal lymph nodes collected postmortem, were analysed to assess the amount of detectable challenge virus. A graphical overview of these results is presented in FIGS. 3 and 4: FIG. 3 represents the results for the animals in groups 1-7 of set 1, receiving a challenge infection with virulent PCV2b virus; FIG. 4 represents the IHC data for all animals of set 2, in which the animals were challenged with virulent PCV2d virus.

The vertical axis presents the score of IHC intensity according to the scale described above. The IHC results can be used to determine the efficacy of the vaccines based on PCV2 ORF2 protein, by comparing the level of reduction of PCV2 infection in vaccinated versus unvaccinated groups.

Several observations could be made:

The unvaccinated animals showed considerably higher IHC scores than the vaccinated groups, indicating that the dose of the challenge was high enough, and that the challenge infection was effective, even in the context of moderate levels of anti-PCV2 maternal antibodies in the piglets.

As can be seen: the vaccine doses comprising 5 or 20 μg ORF2 protein gave strong protection against replication of challenge virus, reaching reduction of IHC scores of up to 90%. Therefore these PCV2 vaccines were highly efficacious.

Somewhat lesser protection was observed for the lowest dose of PCV2a ORF2 protein against PCV2d challenge. This indicates that PCV2 vaccines based on insect-cell expressed mutant ORF2 protein from PCV2b or from PCV2d according to the present invention are very effective as vaccine against PCV2 infection, even at a single dose, and even in the context of maternally derived antibodies. At equal doses, these vaccines based on mutant ORF2 protein from PCV2b or from PCV2d even appeared to be more effective than the traditional vaccine based on PCV2a ORF2 protein.

While homologous protection was mostly better than heterologous protection, there was a clear level of cross-protection against the PCV2b and PCV2d challenge viruses, by all the three vaccine genotypes tested: the PCV2a and PCV2d ORF2 protein vaccines were comparable in protective effect at their lowest dose against PCV2b challenge, while PCV2a ORF2 protein was better at the higher dose. However vaccine based on mutant PCV2b ORF2 protein was better than PCV2a ORF2 protein against PCV2d challenge at both doses.

Figure 1:
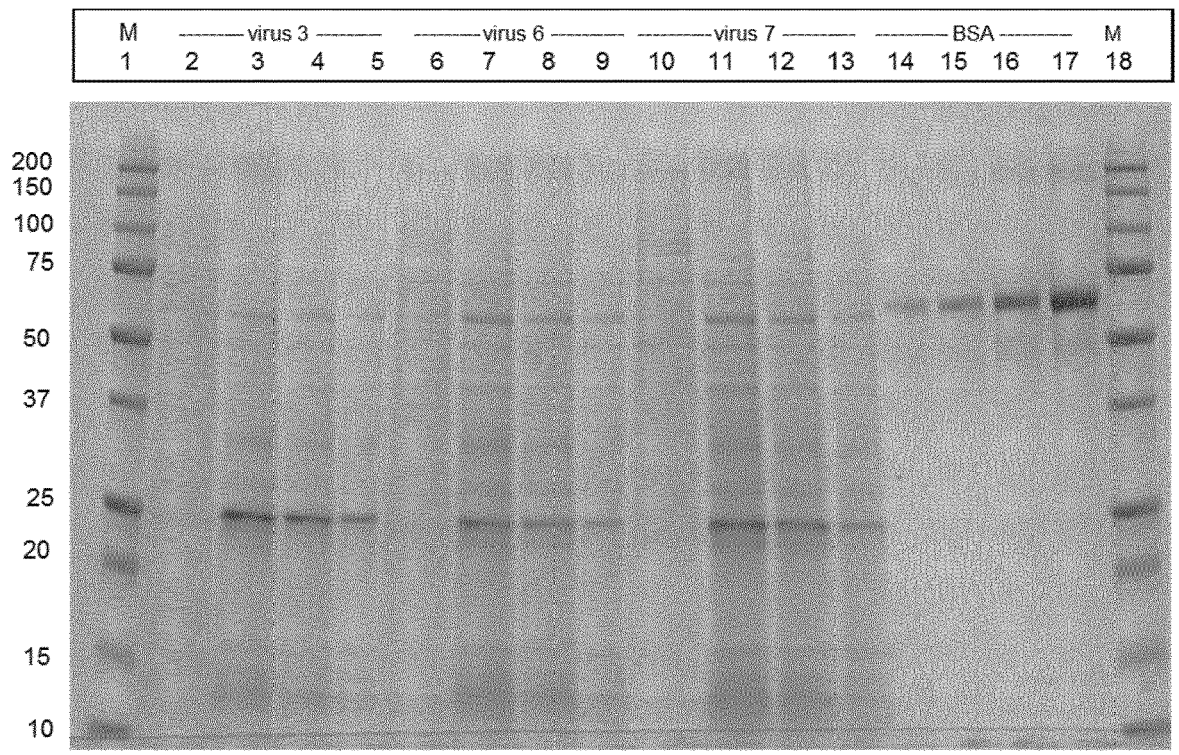
FIG. 1.
Figure 2:
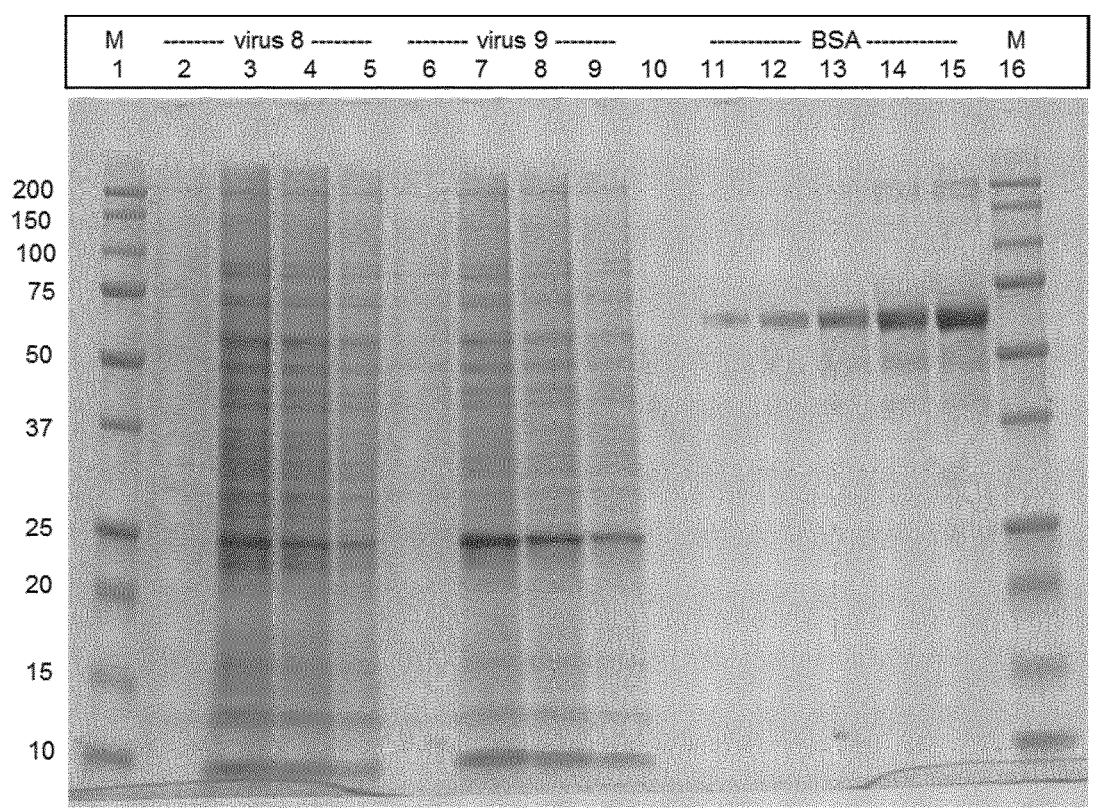

Scan of SDS-PAGE gel with samples from cultures of insect cells expressing different PCV2 ORF proteins via infection with recombinant baculoviruses.

Lane numbers and an indication of the lane content is depicted above the gel image.

Lanes 1 and 18: Molecular weight markers; indications of molecular weights in kDa are indicated to the left of the image Lanes 2-5: cells infected with virus 3; Lane 2: supernatant; Lanes 3-5 cell-pellet, respectively 30, 20, and 10 μl Lanes 6-9: cells infected with virus 6; Lane 6: supernatant; Lanes 7-9 cell-pellet, respectively 30, 20, and 10 μl Lanes 10-13: cells infected with virus 7; Lane 10: supernatant; Lanes 11-13 cell-pellet, respectively 30, 20, and 10 μl Lanes 14-17: reference samples of BSA protein, respectively: 0.25, 0.5, 1, and 2 μg.

FIG. 2:

Scan of SDS-PAGE gel with samples from cultures of insect cells expressing different PCV2 ORF proteins via infection with recombinant baculoviruses.

Lane numbers and an indication of the lane content is depicted above the gel image.

Lanes 1 and 16: Molecular weight markers; indications of molecular weights in kDa are indicated to the left of the image Lanes 2-5: cells infected with virus 8; Lane 2: supernatant; Lanes 3-5 cell-pellet, respectively 30, 20, and 10 μl Lanes 6-9: cells infected with virus 9; Lane 6: supernatant; Lanes 7-9 cell-pellet, respectively 30, 20, and 10 μl Lane 10: empty Lanes 11-15: reference samples of BSA protein, respectively: 0.25, 0.5, 1, 2, and 3 μg.

FIGS. 3 and 4:

Graphical representations of the results from immunohistochemistry on different tissues of pigs that received a challenge infected with PCV2, after receiving a vaccine prepared from insect cell expressed PCV2 ORF2 protein. Tissue results are presented for tonsil, mesenteric lymph nodes ('Mes. ln') and inguinal lymph nodes ('Ing. ln')

The various vaccines applied (or not) are indicated on the horizontal axis; the vertical axis presents the arbitrary score of IHC intensity according to a particular scoring grade.

FIG. 3 represents the IHC results for the animals in groups 1-7 of set 1, receiving a challenge infection with virulent PCV2b virus;

FIG. 4 represents the IHC results for the animals in groups 1-7 of set 2, in which the animals were challenged with virulent PCV2d virus.

The invention claimed is:

1. An insect cell comprising a heterologous nucleic acid comprising:
   a. a nucleotide sequence encoding an ORF2 protein from porcine circovirus 2 of genotype 2b (PCV2b), and
   b. a transcription control sequence that is operatively linked to said nucleotide sequence, wherein the nucleotide sequence encodes a mutant PCV2b ORF2 protein having a Proline at amino acid position number 131.

2. The insect cell of claim 1, wherein the transcription control sequence is selected from the group consisting of a baculovirus p10 gene promoter and a baculovirus polyhedrin gene promoter.

3. The insect cell of claim 1, wherein the heterologous nucleic acid is comprised in a recombinant baculovirus genome.

4. A method of producing a mutant PCV2b ORF2 protein having a Proline at amino acid position number 131, comprising culturing the insect cell of claim 1; wherein the mutant PCV2b ORF2 protein is produced; and whereby an insect cell culture is formed.

5. The method of claim 4, further comprising harvesting the mutant PCV2b ORF2 protein from the insect cell culture.

6. The method of claim 5, wherein said insect cell is a baculovirus-insect cell.

7. The method of claim 4, wherein said insect cell is a baculovirus-insect cell.

8. A virus-like particle (VLP) of a mutant PCV2b ORF2 protein, wherein the mutant PCV2b ORF2 protein has a Proline at amino acid position number 131.

9. A vaccine for porcine animals for reducing infection by PCV2 or reducing associated signs of disease, comprising a mutant PCV2b ORF2 protein in a pharmaceutically acceptable carrier and an adjuvant, wherein the mutant PCV2b ORF2 protein has a Proline at amino acid position number 131.

10. The vaccine of claim 9, wherein the mutant PCV2b ORF2 protein is in the form of a virus-like particle.

11. The vaccine of claim 9, further comprising an antigen from a micro-organism that is pathogenic to porcine animals.

12. A method of reducing an infection by PCV2 or reducing associated signs of disease in a porcine animal, comprising administering to said porcine animal the vaccine of claim 9.

13. A process of preparing a vaccine of claim 9, comprising admixing a mutant PCV2b ORF2 protein having a Proline at amino acid position number 131, with a pharmaceutically acceptable carrier and an adjuvant, thereby forming an admixture.

* * * * *

SEQUENCE LISTING

```
<160> NUMBER OF SEQ ID NOS: 2

<210> SEQ ID NO 1
<211> LENGTH: 702
<212> TYPE: DNA
<213> ORGANISM: Artificial Sequence
<220> FEATURE:
<223> OTHER INFORMATION: PCV2b ORF2 gene - mutated
<220> FEATURE:
<221> NAME/KEY: CDS
<222> LOCATION: (1)..(699)

<400> SEQUENCE: 1 atg acc tac ccc cgt cgt cgt tac cgt cgt cgt cgt cac cgt ccc cgt      48
Met Thr Tyr Pro Arg Arg Arg Tyr Arg Arg Arg Arg His Arg Pro Arg
1               5                   10                  15 agc cat ctg ggc caa atc ctt cgt cgt cgt ccc tgg ctg gtt cac ccc      96
Ser His Leu Gly Gln Ile Leu Arg Arg Arg Pro Trp Leu Val His Pro
```

|  |  |  |  |  |  |  |  |  |  |  |  |  |  |  |  |
|--|--|--|--|--|--|--|--|--|--|--|--|--|--|--|--|
| | | | 20 | | | | 25 | | | | 30 | | | | |

```
cgt cat cgt tac cgt tgg cgt cgt aag aac ggt atc ttc aac acc cgt      144
Arg His Arg Tyr Arg Trp Arg Arg Lys Asn Gly Ile Phe Asn Thr Arg
        35                  40                  45 ctt tca cgt acc ttc gga tac act gtt aag cgt acc act gtg aaa act      192
Leu Ser Arg Thr Phe Gly Tyr Thr Val Lys Arg Thr Thr Val Lys Thr
50                  55                  60 ccc agc tgg gct gtt gac atg atg cgt ttc aac atc aac gac ttc ctt      240
Pro Ser Trp Ala Val Asp Met Met Arg Phe Asn Ile Asn Asp Phe Leu
65                  70                  75                  80 ccc ccc gga ggt gga agc aac ccc cgt tct gtg ccc ttc gag tac tac      288
Pro Pro Gly Gly Gly Ser Asn Pro Arg Ser Val Pro Phe Glu Tyr Tyr
                85                  90                  95 cgt atc cgt aag gtt aaa gtg gaa ttc tgg ccc tgc tct ccc atc acc      336
Arg Ile Arg Lys Val Lys Val Glu Phe Trp Pro Cys Ser Pro Ile Thr
            100                 105                 110 caa ggc gac cgt ggc gtt ggt agc tct gcc gtg atc ctt gac gac aac      384
Gln Gly Asp Arg Gly Val Gly Ser Ser Ala Val Ile Leu Asp Asp Asn
        115                 120                 125 ttc gtt ccc aaa gct acc gcc ctc act tac gac ccc tac gtg aac tac      432
Phe Val Pro Lys Ala Thr Ala Leu Thr Tyr Asp Pro Tyr Val Asn Tyr
130                 135                 140 tca agc cgt cac acc atc act caa ccc ttc tct tac cat tca cgt tac      480
Ser Ser Arg His Thr Ile Thr Gln Pro Phe Ser Tyr His Ser Arg Tyr
145                 150                 155                 160 ttc acc ccc aag ccc gtt ctc gac tct act atc gac tac ttc caa ccc      528
Phe Thr Pro Lys Pro Val Leu Asp Ser Thr Ile Asp Tyr Phe Gln Pro
                165                 170                 175 aac aac aaa cgt aac caa ctg tgg ctt cgt ctc caa acc act ggt aac      576
Asn Asn Lys Arg Asn Gln Leu Trp Leu Arg Leu Gln Thr Thr Gly Asn
            180                 185                 190 gtt gac cac gtg gga ctg ggc acc gct ttc gag aac tca atc tac gac      624
Val Asp His Val Gly Leu Gly Thr Ala Phe Glu Asn Ser Ile Tyr Asp
        195                 200                 205 caa gaa tac aac atc cgt gtt act atg tac gtg caa ttc cgt gag ttc      672
Gln Glu Tyr Asn Ile Arg Val Thr Met Tyr Val Gln Phe Arg Glu Phe
210                 215                 220 aac ctc aag gac ccc ccc ctg aac ccc taa                              702
Asn Leu Lys Asp Pro Pro Leu Asn Pro
225                 230
```

<210> SEQ ID NO 2
<211> LENGTH: 233
<212> TYPE: PRT
<213> ORGANISM: Artificial Sequence
<220> FEATURE:
<223> OTHER INFORMATION: Synthetic Construct

<400> SEQUENCE: 2

```
Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Arg Thr Thr Val Lys Thr
    50                  55                  60

Pro Ser Trp Ala Val Asp Met Met Arg Phe Asn Ile Asn Asp Phe Leu
65                  70                  75                  80
```

-continued

```
Pro Pro Gly Gly Gly Ser Asn Pro Arg Ser Val Pro Phe Glu Tyr Tyr
            85              90              95

Arg Ile Arg Lys Val Lys Val Glu Phe Trp Pro Cys Ser Pro Ile Thr
            100             105             110

Gln Gly Asp Arg Gly Val Gly Ser Ser Ala Val Ile Leu Asp Asp Asn
            115             120             125

Phe Val Pro Lys Ala Thr Ala Leu Thr Tyr Asp Pro Tyr Val Asn Tyr
    130             135             140

Ser Ser Arg His Thr Ile Thr Gln Pro Phe Ser Tyr His Ser Arg Tyr
145             150             155             160

Phe Thr Pro Lys Pro Val Leu Asp Ser Thr Ile Asp Tyr Phe Gln Pro
            165             170             175

Asn Asn Lys Arg Asn Gln Leu Trp Leu Arg Leu Gln Thr Thr Gly Asn
            180             185             190

Val Asp His Val Gly Leu Gly Thr Ala Phe Glu Asn Ser Ile Tyr Asp
        195             200             205

Gln Glu Tyr Asn Ile Arg Val Thr Met Tyr Val Gln Phe Arg Glu Phe
        210             215             220

Asn Leu Lys Asp Pro Pro Leu Asn Pro
225             230
```